US012807580B2

(12) United States Patent
Siri et al.

(10) Patent No.: US 12,807,580 B2
(45) Date of Patent: Nov. 24, 2026

(54) PHENAZINE DERIVATIVE AND USE THEREOF FOR THE TREATMENT OF CANCER

(71) Applicants: CENTRE NATIONAL DE LA RECHERCHE SCIENTIFIQUE, Paris (FR); UNIVERSITE D'AIX-MARSEILLE, Marseilles (FR)

(72) Inventors: Olivier Siri, Belcodene (FR); Zhongrui Chen, Beijing (CN)

(73) Assignees: CENTRE NATIONAL DE LA RECHERCHE SCIENTIFIQUE, Paris (FR); UNIVERSITE D'AIX-MARSEILLE, Marseilles (FR)

(*) Notice: Subject to any disclaimer, the term of this patent is extended or adjusted under 35 U.S.C. 154(b) by 1304 days.

(21) Appl. No.: 17/639,540

(22) PCT Filed: Sep. 2, 2020

(86) PCT No.: PCT/EP2020/074447

§ 371 (c)(1),
(2) Date: Mar. 1, 2022

(87) PCT Pub. No.: WO2021/043813

PCT Pub. Date: Mar. 11, 2021

(65) Prior Publication Data

US 2022/0315539 A1 Oct. 6, 2022

(30) Foreign Application Priority Data

Sep. 2, 2019 (FR) ...................................... 1909642

(51) Int. Cl.
*C07D 241/46* (2006.01)
*A61P 35/00* (2006.01)
*G01N 33/57515* (2026.01)

(52) U.S. Cl.
CPC ............ *C07D 241/46* (2013.01); *A61P 35/00* (2018.01); *G01N 33/57515* (2026.01)

(58) Field of Classification Search
None
See application file for complete search history.

(56) References Cited

U.S. PATENT DOCUMENTS

2004/0065227 A1 4/2004 Breton et al.

FOREIGN PATENT DOCUMENTS

| | | | |
|---|---|---|---|
| EP | 2368885 | A1 | 9/2011 |
| WO | 2007016762 | A1 | 2/2007 |
| WO | 2010129340 | A2 | 11/2010 |
| WO | 2011117830 | A1 | 9/2011 |

OTHER PUBLICATIONS

Liu, Y., Jin, L., and Liu, J.-f. (2017) A New Route for Synthesis of 2-Substituted-3-amino-5-phenyl-7-N,N-dimethylamino Phenazinium Chloride Salts. J. Heterocyclic Chem., 54: 1931-1936. doi: 10.1002/jhet.2788 (Year: 2017).*

International Search Report mailed on Nov. 16, 2020, in corresponding to International Application No. PCT/EP2020/074447; 9 pages (with English Translation).

Suman K Roy et al, "Aerial Oxidation of Protonated Aromatic Amines, Isolation, X-ray Struture, and Redox and Spectral Characteristics of N-Containing Dyes"; Journal of Organic Chemistry; vol. 77; No. 22; Oct. 30, 2012; XP055743275; pp. 10249-10259.

Lantz, Robert et al., "Oxidative condensation of "Willstaetter emeraldine" with aniline. Analogous reactions leading to aniline black and structures of these dyes"; 1965; retrieved from STN, Abstract No. Database accession No. 1965:410701; XP002800819.

Miura, Sadami et al., "Manufacture of composite polyester films with good regulation properties of electric charge"; 1996; retrieved from STN; Abstract No. Database accession No. 1996:128301; XP002800820; Abstract Only.

Chemical Abstracts Service; Aug. 29, 2004; Abstract No. Database accession No. 735245-74-6; XP002800821; Abstract.

Jean-Luc Pozzo et al., "Rational design of new acid-sensitive organogelators"; Journal of Materials Communication Chemistry; vol. 8; 1998; pp. 2575-2577.

Jane Buus Laursen et al., "Phenazine Natural Products: Biosynthesis, Synthetic Analogues, and Biological Activity"; American Chemical Society; Chemical Review; 2004; vol. 104; No. 3; pp. 1663-1685.

Uwe Beifuss et al., "Methanophenazine and Other Natural Biologically Active Phenazines"; Top Curr Chem 2005; vol. 244; pp. 77-113.

Mario Llusar et al., "One-pot synthesis of phenyl- and amine-functionalized silica fibers through the use of anthracenic and phenazinic organogelators"; Journal of Materials Chemistry; 2003; vol. 13; pp. 2505-2514.

Mario Llusar et al., "Grafting of Gold Nanoparticles onto Organogelator-Templated Fibrous Mercaptosilica"; Z. Anorg. Allg. Chem. 2005; vol. 631; pp. 2215-2220.

(Continued)

*Primary Examiner* — Samantha L Shterengarts

(74) *Attorney, Agent, or Firm* — Maier & Maier, PLLC

(57) ABSTRACT

A compound of formula (I), (I)

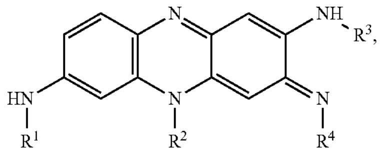

wherein $R^1$, $R^2$, $R^3$ and $R^4$ are selected from a saturated or unsaturated, branched or unbranched, cyclic or non-cyclic alkyl, or an amide, or a functional group, or a salt or a solvate thereof, or a protonated form thereof, and to the use thereof for the treatment of cancer.

11 Claims, 10 Drawing Sheets

(56) References Cited

OTHER PUBLICATIONS

J.L. Pozzo et al., "Photchromic Guests in Organogels"; Molecular Crystals and Liquid Crystals Science and Technology; Molecular Crystals and Liquid Crystals; 2000; vol. 344; pp. 101-106.

Pierre Terech et al., "Structural variations in a family of orthodialkoxyarenes organogelators"; ScienceDirect; Elsevier; Journal of Colloid and Interface Science; 2006; vol. 302; pp. 633-642.

* cited by examiner

[Fig. 1]
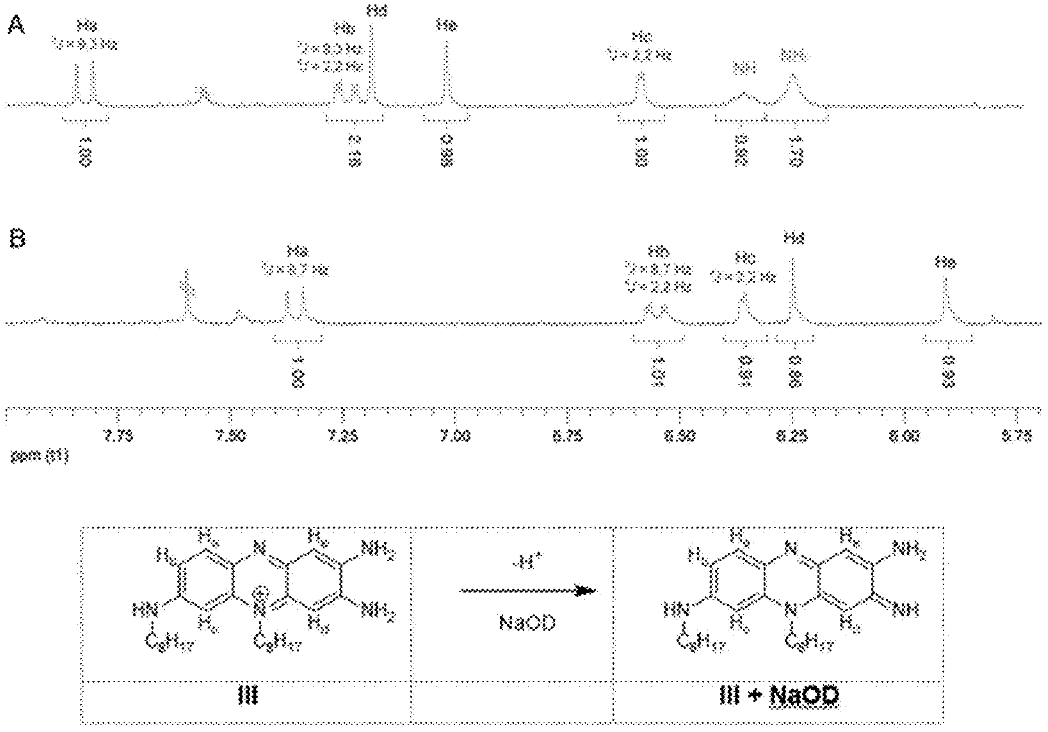
[Fig. 2]
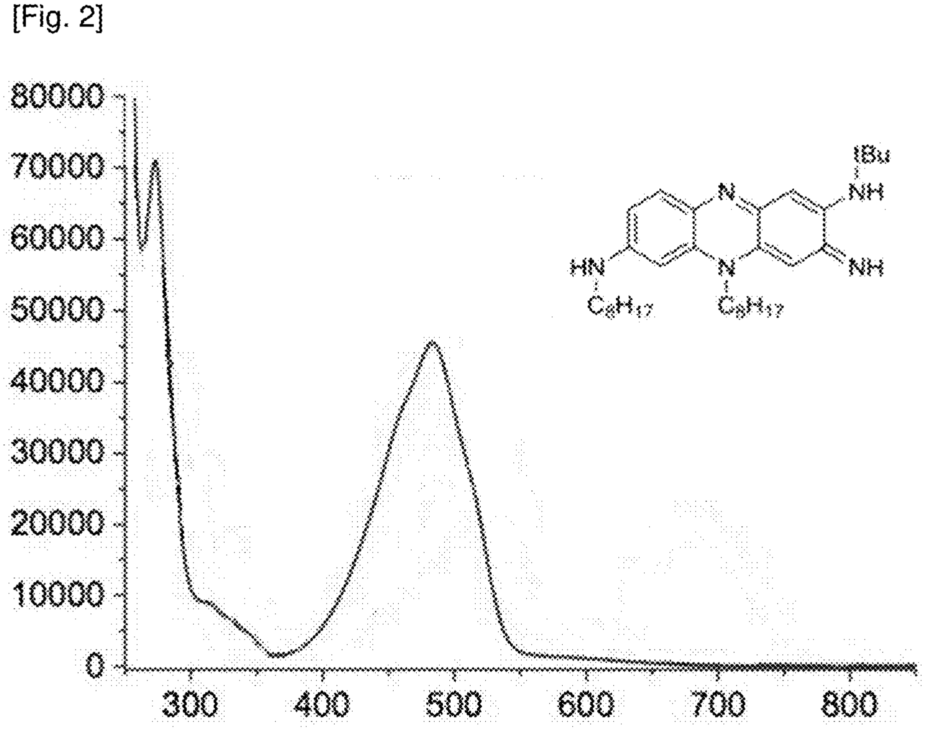

[Fig. 3]
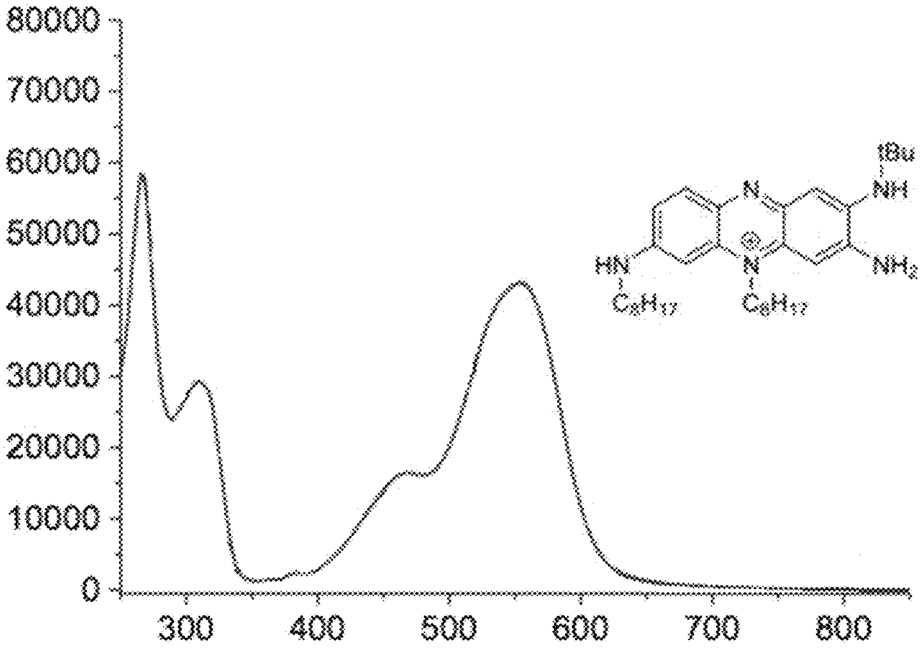
[Fig. 4]
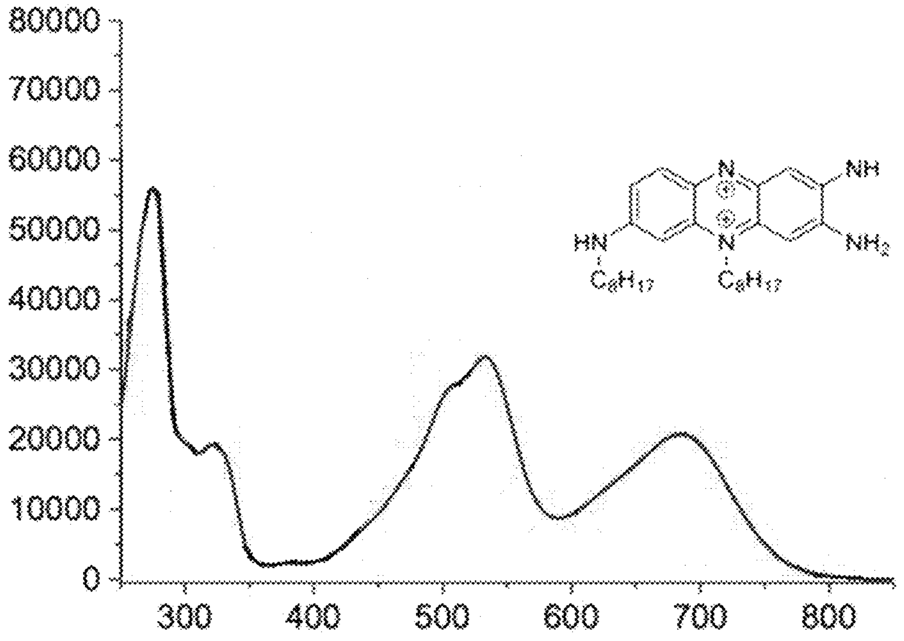

[Fig. 5]
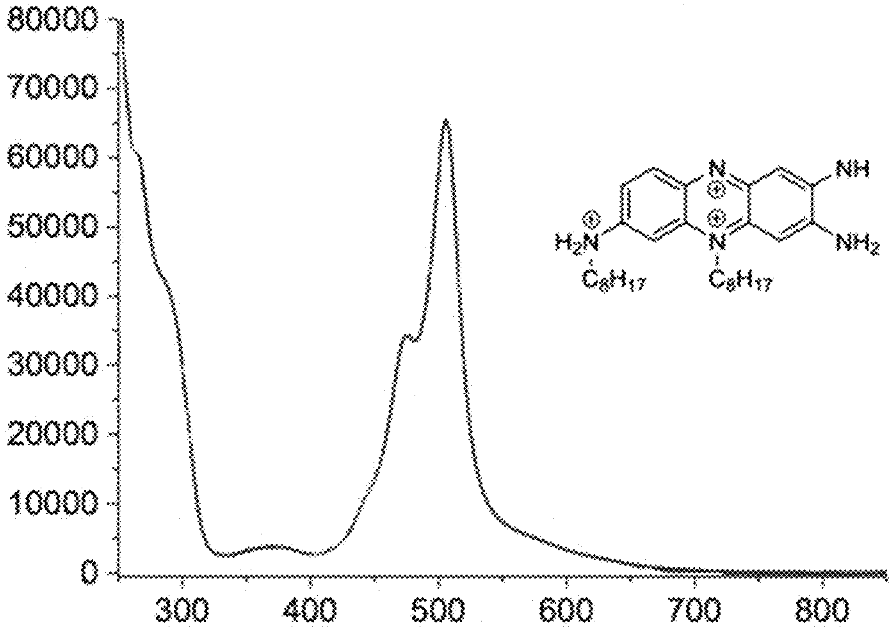
[Fig. 6]
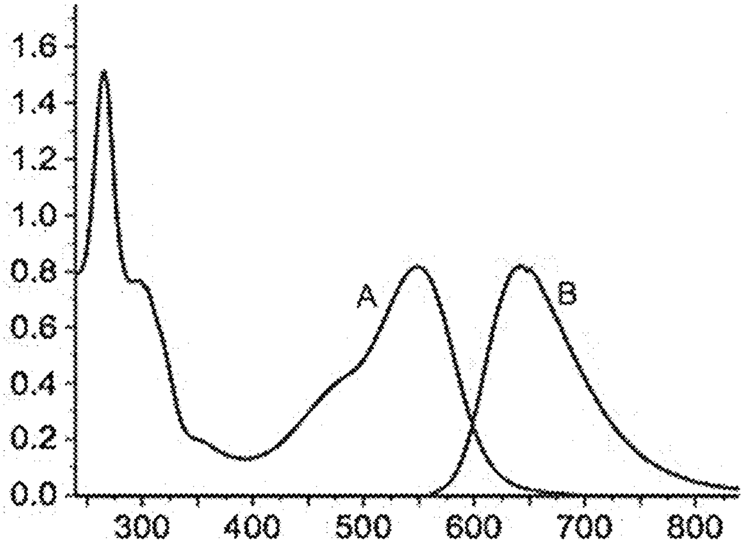

[Fig. 7]
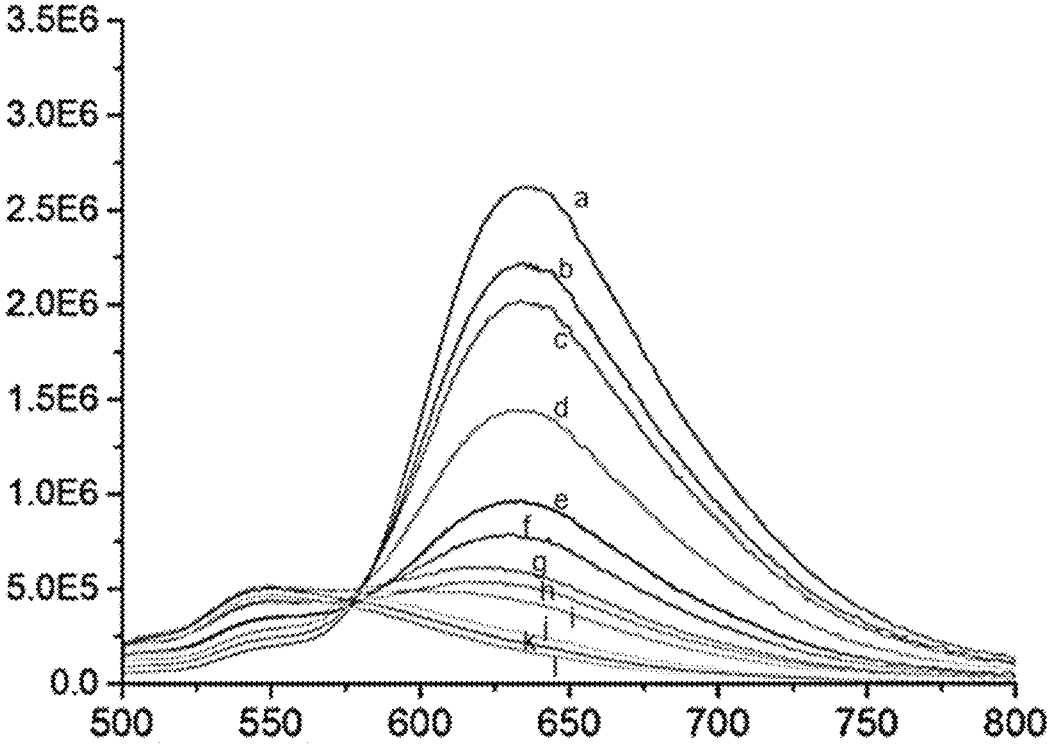
[Fig. 8]
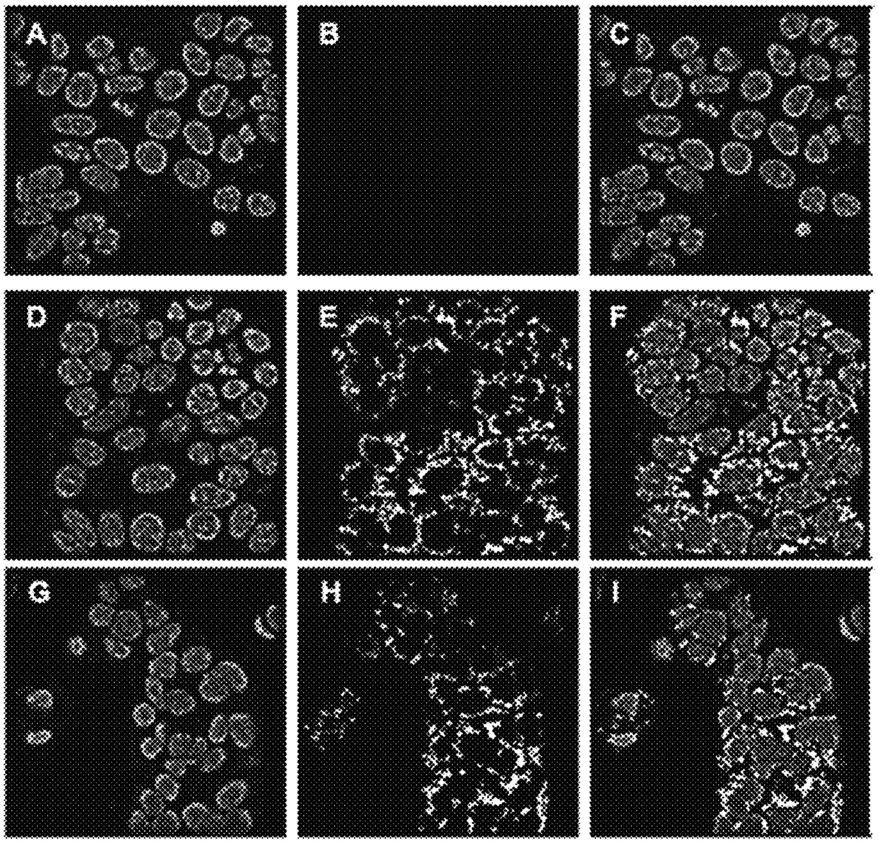

[Fig. 9]
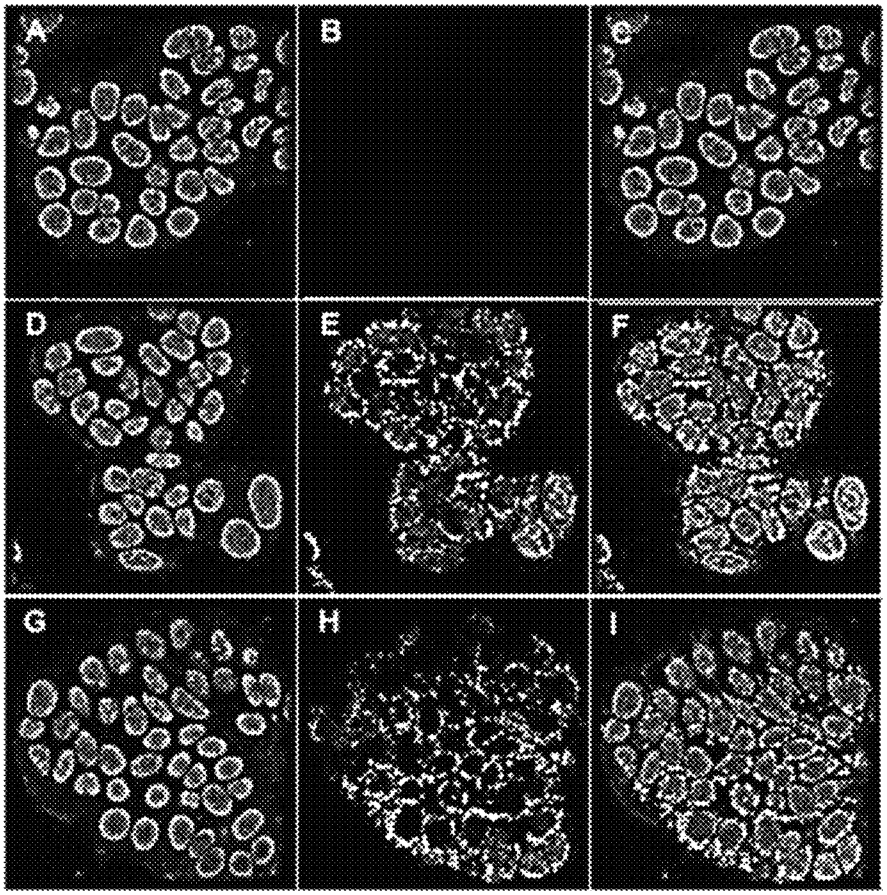
[Fig. 10]
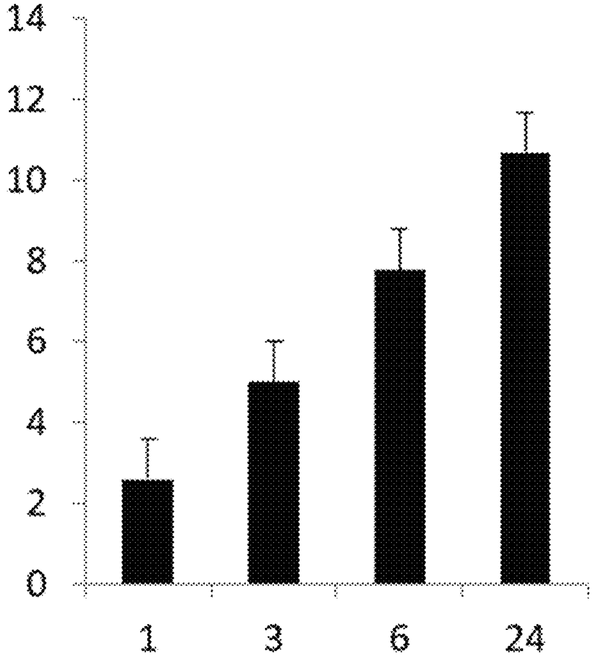

[Fig. 11]
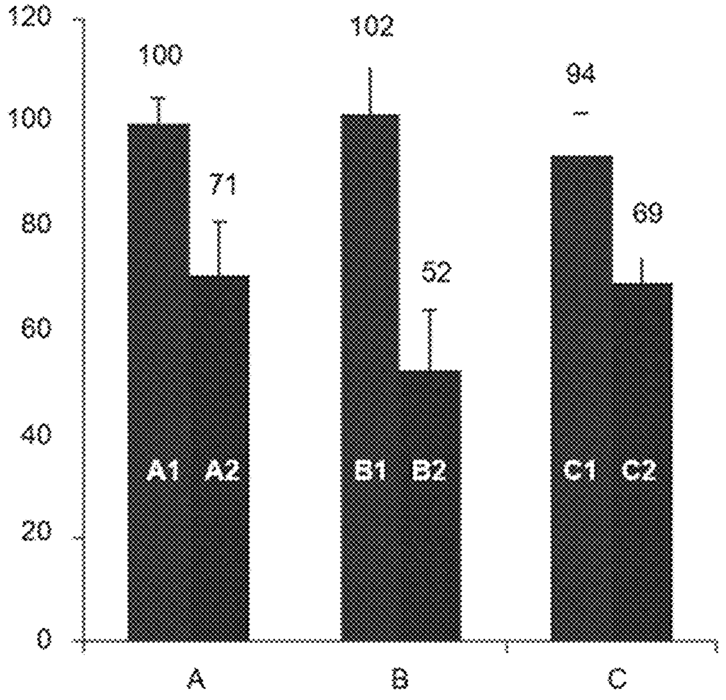
[Fig. 12]
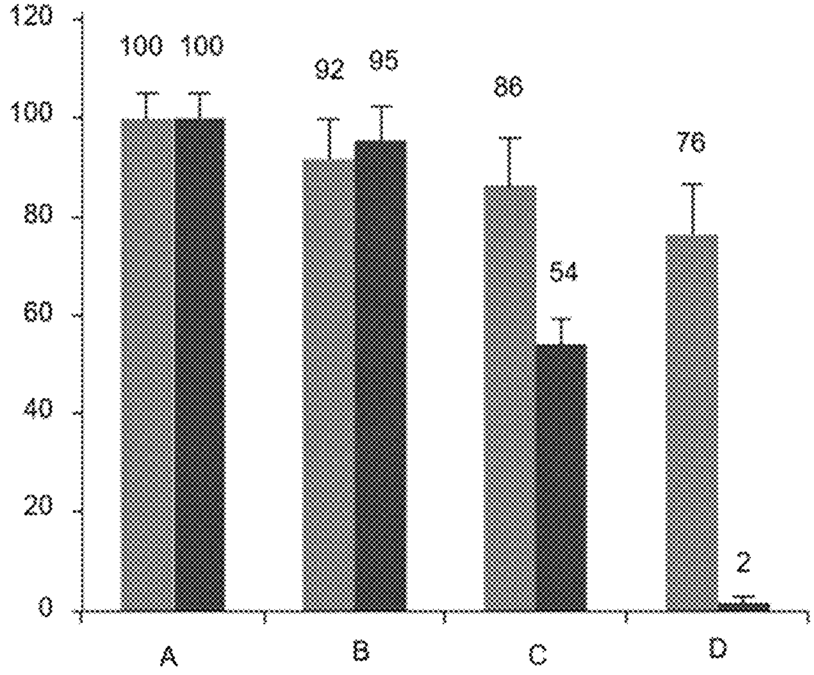

[Fig. 13]
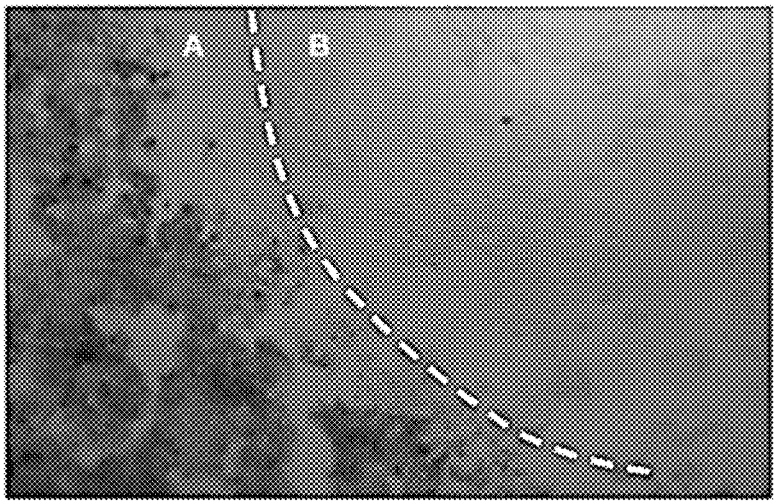
[Fig. 14]
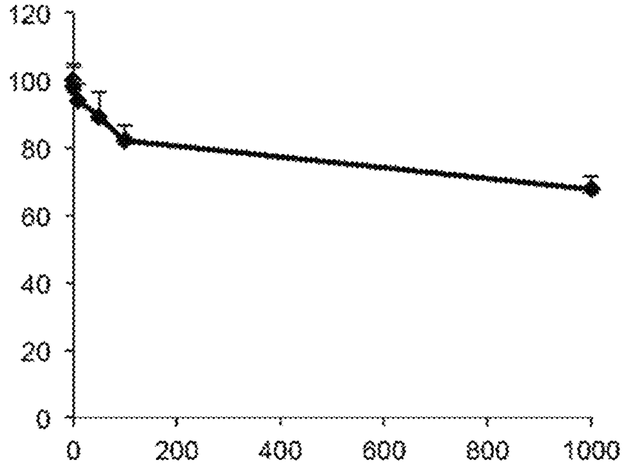
[Fig. 15]
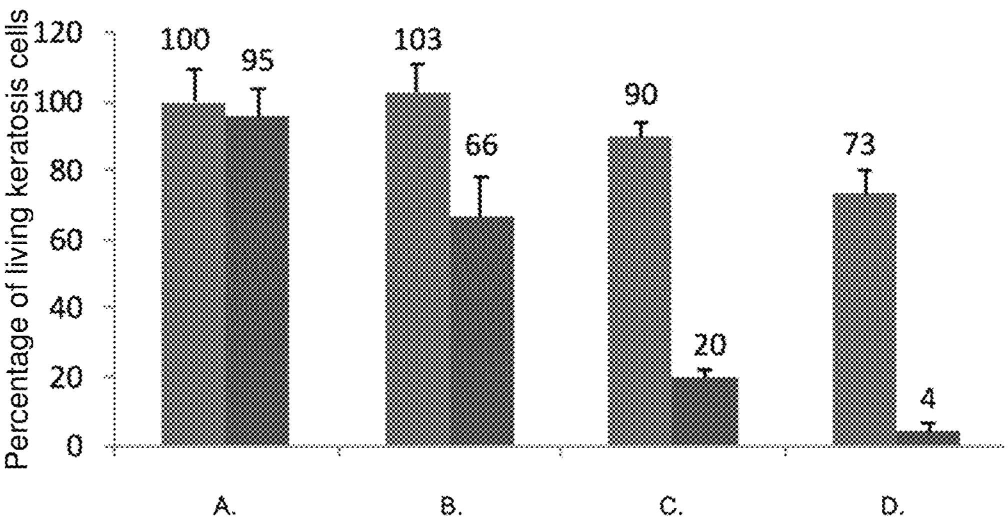

[Fig. 16]
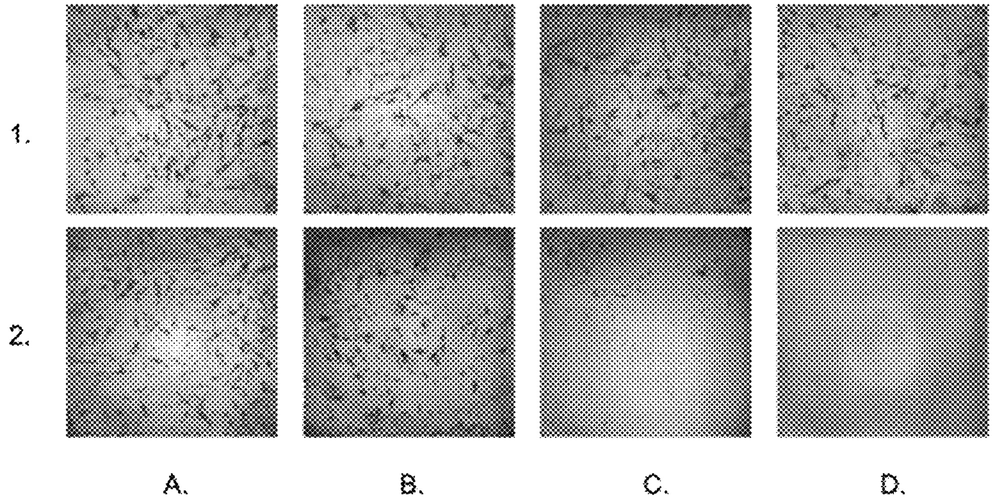
[Fig. 17]
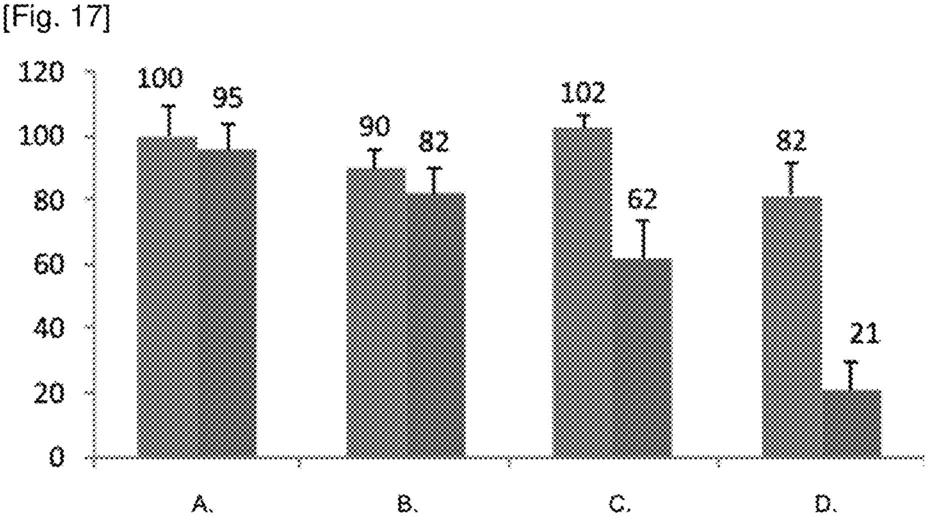
[Fig. 18]
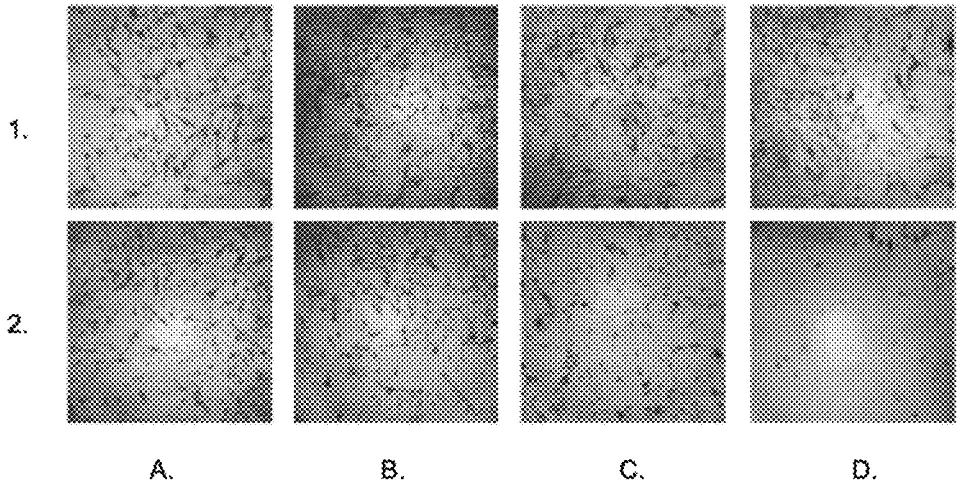

[Fig. 19]
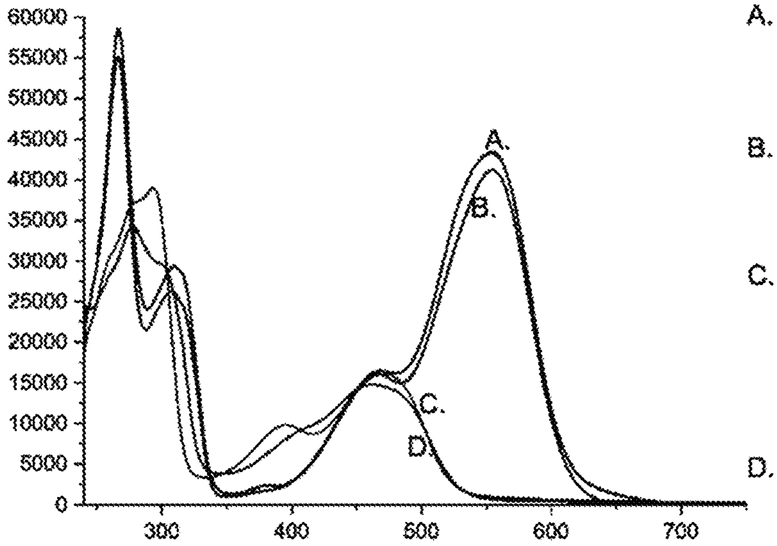
A.
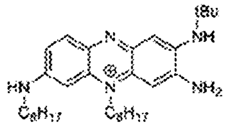
B.
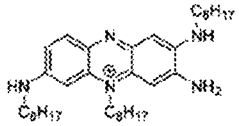
C.
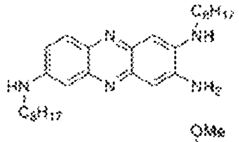
D.
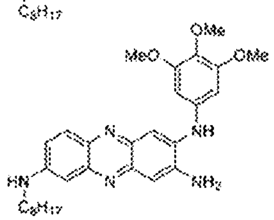
[Fig. 20]
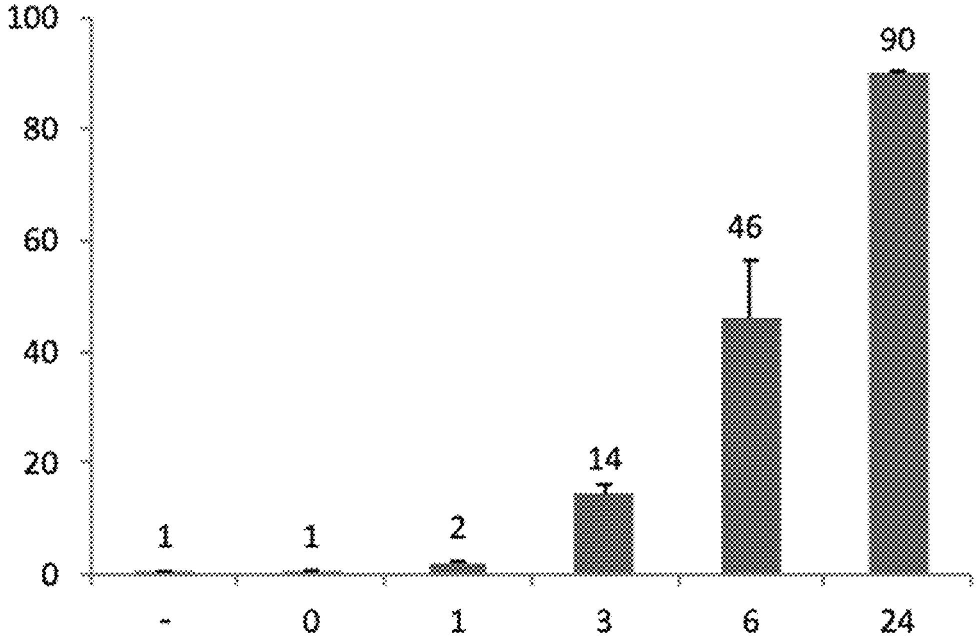

[Fig. 21]
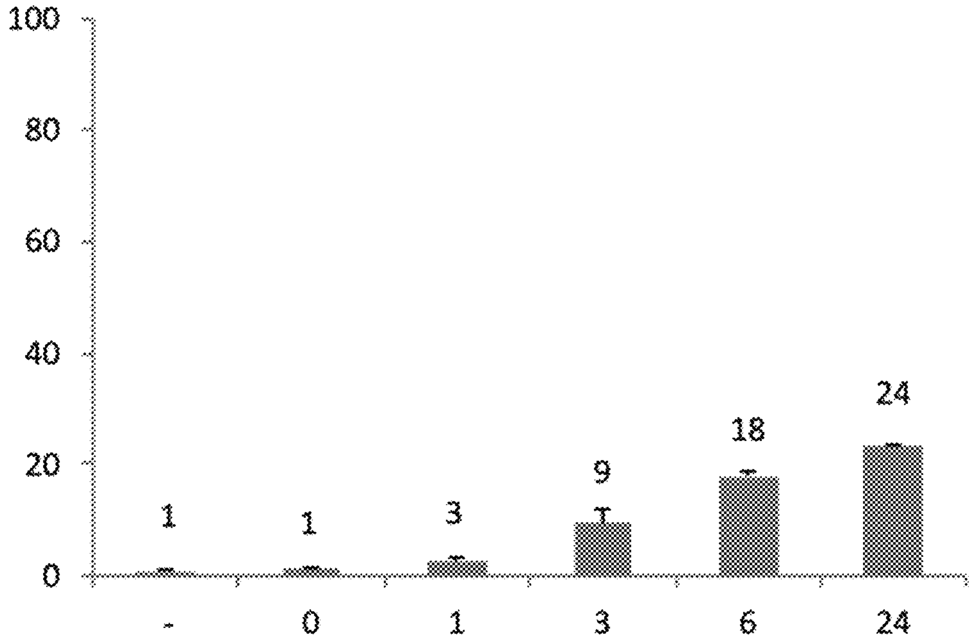

PHENAZINE DERIVATIVE AND USE THEREOF FOR THE TREATMENT OF CANCER

FIELD

The invention relates to phenazine derivatives and uses thereof, in particular therapeutic uses thereof.

BACKGROUND

In the context of the treatment of pathologies and in particular tumors, new molecules and new approaches are constantly being developed and tested.

In particular, in recent years, photodynamic therapy has experienced a boom in particular for the treatment of skin pathologies. However, the sensitizing compounds known to date do not exhibit the best effects, and the failure rates are quite high. In addition, the wavelengths of the lasers used may generate adverse effects and induce deep lesions of the exposed tissues.

There is therefore a need to provide new compounds that would be effective for this type of non-invasive therapy.

One approach is to use fluorescent compounds capable of specifically targeting the cells of interest and exhibiting therapeutic properties under activation.

However, such compounds are rare.

Some phenazine derivatives are already known. Various compounds having such a phenazine structure have already been described in Laursen et al (chem Rev, 2004, 104:1663), Beifuss et al (above. Curr. Chem, 2005,77), Terech et al (J Of Coll. Et entre. Sc, 2006:633), Llusar et al (Zeit. Fuer Anorg. Und Allge, chem, 2005, 631:2215; J Of Mat. Chem, 2003, 13:2505), Pozzo et al (Mol. Les cristaux et les Cristaux liquids Sc Et Tech, 2000, 344:101; J Of Mat. Chem, 1998, 8:2575) and US 2004/065227. However, to the knowledge of the inventors, these compounds have never been proposed as chemotherapeutic agents. In addition, patent application WO2011117830 describes compounds derived from phenazine, but here again, to the knowledge of the inventors, such compounds do not have properties known to be used in photodynamic therapy.

SUMMARY

There is therefore still a need for new compounds, and the invention aims to overcome this lack.

One of the aims of the invention is to provide compounds that can be used in photodynamic therapy that are effective, inexpensive and easy to produce.

Another object of the invention is to provide various therapeutic and diagnostic uses of these new compounds.

The invention relates to a compound of the following formula I:

[Chem. 1]

(I)

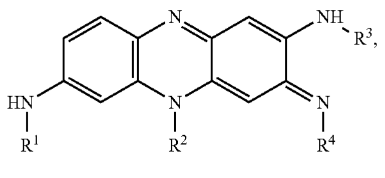

where, independently of each other, R1 and R2 are

- either a linear or branched, saturated or unsaturated, cyclic or non-cyclic C1-C18 alkyl, optionally substituted by one or more groups chosen from a hydroxyl group, an amino group, an aminoalkyl group, a C1-C5 alkoxy group, a C1-C5 alkyl, a peptide, a pyridine group, a phosphine group, a thiol, a C2 alkene, a C2 alkyne group and a halogen, or a benzyl radical optionally substituted by one or more radicals chosen from a hydroxyl group, an amino group, an aminoalkyl group, a C1-C5 alkoxy group, a C1-C5 alkyl group, and a halogen atom,
- or (hetero) aryl groups, optionally substituted by one or more groups chosen from a hydroxyl group, an amino group, an aminoalkyl group, a C1-C5 alkoxy group, a C1-C5 alkyl, a peptide, a pyridine group, a phosphine group, a thiol, a C2 alkene, a C2 alkyne group and a halogen, or a benzyl radical optionally substituted by one or more radicals chosen from a hydroxyl group, an amino group, an aminoalkyl group, a C1-C5 alkoxy group, a C1-C5 alkyl group, and a halogen, in particular R2 possibly being a hydrogen atom, and independently of each other, R3 and R4 are hydrogen H or correspond to R1 or R2 mentioned above, or R3 and R4 are either or both a carbonyl functional group forming amide functions including peptides or not, or a salt or solvate thereof, or a protonated form thereof.

The invention is based on the surprising observation by the inventors that the aforementioned phenazine derivatives have variable fluorescent properties depending on the degree of protonation for in vitro and in vivo studies with an imaging objective. These molecules may also be used in the context of photodynamic therapy (PDT), with one and two photons.

BRIEF DESCRIPTION OF THE DRAWINGS

FIG. 1 1H NMR spectra of I in MeCN-d3: without added NaOD (A), with added NaOD (B) (the window between δ=5.7 ppm and 0 ppm was omitted for reasons of clarity): The table indicates the protonated form and the non-protonated form in the presence of NaOD. The x-axis represents values in ppm.

FIG. 2 shows the absorption spectrum ε (M-1 cm-1) as a function of the wavelength λ (in nm) of the compound shown.

FIG. 3 shows the absorption spectrum ε (M-1 cm-1) as a function of the wavelength λ (in nm) of the compound shown.

FIG. 4 shows the absorption spectrum ε (M-1 cm-1) as a function of the wavelength λ (in nm) of the compound shown.

FIG. 5 shows the absorption spectrum ε (M-1 cm-1) as a function of the wavelength λ (in nm) of the compound shown.

FIG. 6 shows the absorption spectrum (A) as a function of the wavelength A (in nm) and the emission spectrum (B) as a function of the wavelength λ (in nm) of the following compound in acetonitrile:

[Chem. 5]

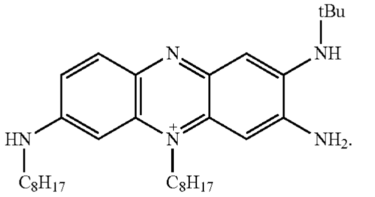

FIG. 7 shows the emission spectrum as a function of the wavelength λ (in nm) of the following compound in acetonitrile:

[Chem. 5]

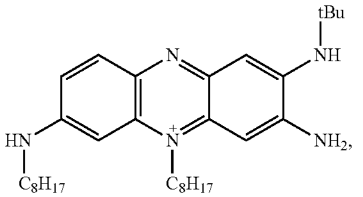

in the presence of 0 DBU equivalents (a), 0.1 DBU equivalents (b), 0.2 DBU equivalents (c), 0.4 DBU equivalents (d), 0.6 DBU equivalents (e), 0.8 DBU equivalents (f), 1.0 DBU equivalents (g), 1.2 DBU equivalents (h), 1.4 DBU equivalents (i), 1.6 DBU equivalents (j), 1.8 DBU equivalents (k), 2.5 DBU equivalents (I).

FIG. 8 shows the capture of the compound of formula

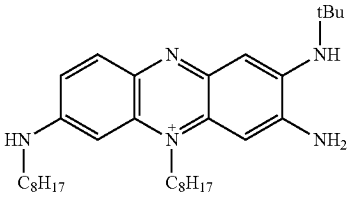

by human breast cancer cells (MCF-7). The MCF-7 cells were incubated for 16 h with the compound at concentrations of 0 µM (B), 0.1 µM (E) or 0.5 UM (H). The nuclei were stained with Hoechst 33342 (A, D and G). Single-photon fluorescence imaging was performed on live cells at the excitation wavelength of 514 nm with a Carl Zeiss microscope. Images C, F, and I represent the superposition of the signals of images A+B, D+E and G+H, respectively.

FIG. 9 shows the capture of the compound of formula

[Chem. 5]

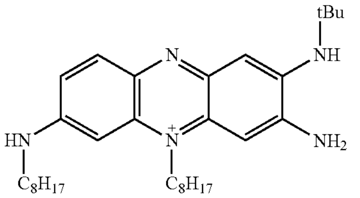

by human breast cancer cells (MCF-7). The MCF-7 cells were incubated for 16 h with the compound at concentrations of 0 µM (B), 0.5 UM at 790 nm (E) or 0.5 µM at 810 nm (H). The nuclei were stained with Hoechst 33342 (A, D and G). Single-photon fluorescence imaging was performed on live cells at the excitation wavelengths of 790 or 810 nm with a Carl Zeiss microscope. Images C, F, and I represent the superposition of the signals of images A+B, D+E and G+H, respectively.

FIG. 10 shows the incorporation kinetics of the compound depicted in FIG. 8 using a CLARIOstar plate reader to quantify internalization. Data are percent internalization (remaining fluorescence/total fluorescence) as a function of time in hours. Data are means of three experiments±standard deviation.

FIG. 11 shows the survival of MCF7 cells incubated for 5 hours with the compound described in FIG. 9 at a concentration of 0.5 M, without irradiation (A2), after irradiation at 790 nm (B2) or 810 nm (C2). As a control, untreated MCF7 cells without irradiation (A1), after irradiation at 790 nm (B1) or 810 nm (C1) are presented. The y-axis shows the percentage of live MCF-7 cells (numbered values are indicated above each bar). Data are means of three experiments±standard deviation.

FIG. 12 is a bar graph showing the effectiveness of single-photon photodynamic therapy at 540 nm. MCF-7 cells were incubated with the compound for 5 h at doses of 0 nM (A), 1 nM (B), 10 nM (C) or 100 nM (D) and irradiated (black columns) or not (gray columns) at 530 nm for 20 minutes. Two days later, the cells were subjected to a colorimetric cell viability assay (MTT). The experiment was carried out 3 times. The y-axis shows the percentage of live MCF-7 cells.

FIG. 13 shows a photo of the junction zone between MCF-7 cells treated with the compound at 100 nM and irradiated at 540 nm (B) or not (A). The living cells are visible owing to the purple marking following the MTT treatment.

FIG. 14 shows a graph illustrating the percentage of MCF-7 cells after treatment for 72 hours with a compound according to the invention at the doses indicated. Data are means of three experiments±standard deviation.

FIG. 15 is a bar graph showing the effectiveness of single-photon photodynamic therapy at 540 nm. Keratosis cells were incubated with the compound of formula

[Chem. 5]

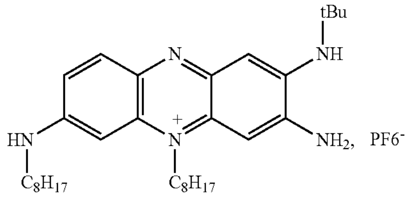

for 20 min at doses of 0 nM (A), 10 nM (B), 25 nM (C) or 50 nM (D) and irradiated (black columns) or not (grey columns) at 530 nm. Two days later, the cells were subjected to a colorimetric cell viability assay (MTT). The experiment was carried out 3 times. The y-axis represents the percentage of living keratosis cells.

FIG. 16 shows the photos of the area not treated with the laser (1.) or treated with the laser (2.) at doses of 0 nM (A), 10 nM (B), 25 nM (C) or 50 nM (D) of compound of formula

[Chem. 5]

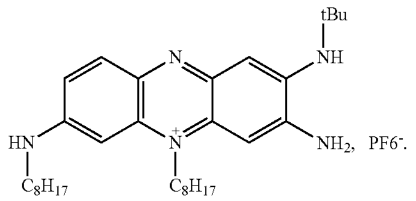

FIG. 17 is a bar graph showing the effectiveness of single-photon photodynamic therapy at 540 nm. Keratosis cells were incubated with the compound of formula:

[Chem. 6]

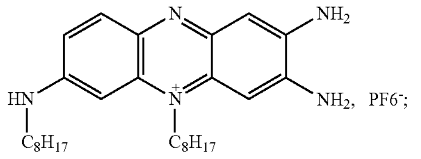

for 20 min h at doses of 0 nM (A), 10 nM (B), 25 nM (C) or 50 nM (D) and irradiated (black columns) or not (grey columns) at 530 nm. Two days later, the cells were subjected to a colorimetric cell viability assay (MTT). The experiment was carried out 3 times. The y-axis represents the percentage of living keratosis cells.

FIG. 18 shows the photos of the area not treated with the laser (1.) or treated with the laser (2.) at doses of 0 nM (A), 10 nM (B), 25 nM (C) or 50 nM (D) of compound of formula:

[Chem. 5]

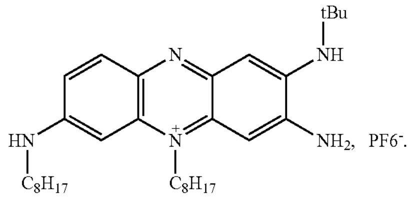

FIG. 19 shows the absorption spectra of the *phenazinium* compounds according to the invention (A and B) and of the phenazine compounds (C and D).

FIG. 20 shows a graph illustrating the internalization of the compound of formula

[Chem. 5]

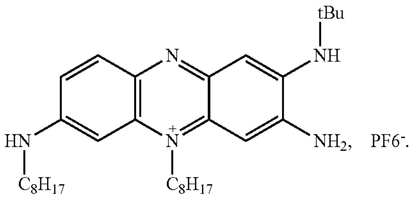

by live MCF-7 cancer cells. Cells were treated with 0.5 nM compound for 1, 3, 6 or 24 h and red fluorescence was measured by flow cytometry. The results show the mean of two experiments+/− the standard deviation. The x-axis represents the incubation time in hours and the y-axis the percentage of red fluorescent cells.

FIG. 21 shows a graph illustrating the internalization of the compound of formula

[Chem. 5]

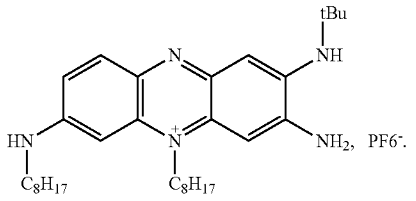

by healthy living cells of the fibroblast type. Cells were treated with 0.5 nM compound for 1, 3, 6 or 24 h and red fluorescence was measured by flow cytometry. The results show the mean of two experiments+/− the standard deviation. The x-axis represents the incubation time in hours and the y-axis the percentage of red fluorescent cells.

DETAILED DESCRIPTION

Thus, the present invention describes a family of original compounds, low in toxicity and particularly promising for one- and two-photon imaging depending on the desired target. Their synthesis is carried out in few steps and at low cost. The intensity of the markings is remarkable, which objectively allows a more precise identification of the cytoplasmic targets to be envisaged. The intense fluorescence foci obtained in perinuclear regions could in particular correspond to the localization of the probe at the endoplasmic reticulum. These compounds therefore allow a crucial advance to be envisaged in the field of selective imaging and photodynamic therapy.

As will be demonstrated hereinafter in the examples, these compounds have allowed in vitro studies to be carried out on human cancer cells known to be a good model of xenograft, and one- and two-photon photon therapy have been shown to be effective in destroying such cells.

According to the present invention, the terms below have the following meanings, and the terms mentioned here having characteristics such as C1-C18, for example, can also be used with lower numbers of carbon atoms such as C1-C3 or C1-C5. If for example the term C1-C5 is used, it means that the corresponding hydrocarbon chain can comprise from 1 to 5 carbon atoms. If for example the term C3-C8 is used, it means that the corresponding hydrocarbon chain or ring can comprise from 3 to 8 carbon atoms.

A C1-C18 alkyl according to the invention is an alkyl comprising 1, 2, 3, 4, 5, 6, 7, 8, 9, 10, 11, 12, 13, 14, 15, 16, 17 or 18 carbon atoms.

“Alkyl” means a saturated, linear or branched aliphatic group. Examples include: methyl, ethyl, 1-propyl, 2-propyl, 1-butyl, 2-methyl-1-propyl (also called i-Bu), 2-butyl (also called s-Bu), 2-methyl-2-propyl (also called t-Bu), 1-pentyl (also called n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-pentyl, n-hexyl, n-heptyl, H-octyl, n-nonyl, n-decyl, n-undecyl, n-dodecyl, n-tridecyl, n-tetradecyl, n-pentadecyl, n-hexadecyl, n-heptadecyl, n-octadecyl. The preferred alkyl according to the invention is methyl, ethyl, 1-propyl, 2-propyl, 1-butyl, 2-methyl-1-propyl (also called i-Bu), 2-butyl (also called s-Bu), 2-methyl-2-propyl (also called t-Bu), 1-pentyl (also called n-pentyl), 2-pentyl, 3-pentyl, 2-methyl-2-butyl, 3-methyl-2-butyl, 3-methyl-1-butyl, 2-methyl-1-butyl.

The term “hydroxyl” corresponds to an alkyl-OH group, the alkyl group being as defined above.

The term “amino” corresponds to an amine which can be secondary, tertiary or quaternary. By extension, an “aminoalkyl” corresponds to an alkyl substituted by an amine.

The term “alkoxy” corresponds to an-O-alkyl group, the alkyl group being as defined above. The following examples may be cited: methoxy (i.e. C1 alkoxy), ethoxy (i.e. C2 alkoxy), propoxy (i.e. C3 alkoxy), isopropoxy (i.e. C4 alkoxy).

The term “halogen atom” corresponds to a fluorine, chlorine, bromine or iodine atom. Chlorine is a preferred halogen atom within the scope of the present invention.

The term “halogen atom” corresponds to a fluorine, chlorine, bromine or iodine atom. Chlorine and fluorine are preferred halogen atoms within the scope of the present invention.

The term “aryl” used herein means a mono- or poly-cyclic aromatic group. An example of a monocyclic group can be phenyl.

The compounds of formula (I) possess unsaturations and can thus be in their tautomeric form. The present invention therefore also relates to the compounds of formula (I) in their tautomeric form.

The compounds of formula (I) may be in the form of a free base or in the form of addition salts with acids, which also form part of the invention.

These salts can be prepared with pharmaceutically acceptable acids, but additionally salts with other acids, useful for example to purify or isolate the compounds of formula (I), also form part of the invention.

Advantageously, the invention relates to the aforementioned compounds where R1 and R2 are, in particular independently of one another, linear or branched, saturated or unsaturated, cyclic or non-cyclic C4-C10 alkyls.

Examples of saturated linear alkyls are butyl, pentyl, hexyl, heptyl, octyl, nonyl and decyl groups.

Examples of saturated linear branched alkyls are isobutyl, sec-butyl, tert-butyl, isopentyl, neopentyl, tert-pentyl, 1-methyl isobutyl, 2,3-dimethylpentane, 2-methylpropane, 2-methylbutane, 2-methylpentane, 2-ethylbutane, 3-methylpropane, 3-methylbutane, 3-methylpentane More advantageously, the invention relates to the aforementioned compound, where the protonated form of the compound of formula I is chosen from the following compounds:

the compound of formula Ia:

[Chem. 2]

(Ia)

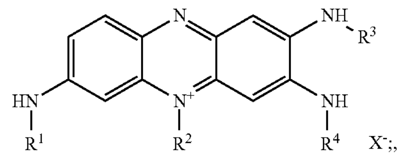

the compound of formula Ib:

[Chem. 3]

(Ib)

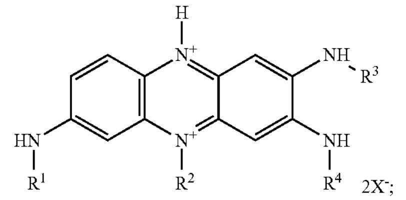

and the compound of formula Ic:

[Chem. 4]

(Ic)

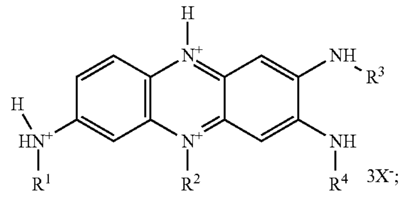

where X represents Cl, Br, OH, F, I, $BF_4$ or $PF_6$ or trifluoromethanesulfate (Otf).

The compounds of formula Ia are the most advantageous compounds according to the invention.

Thus, advantageously the invention relates to a compound of the following formula Ia:

[Chem. 2]

(Ia)

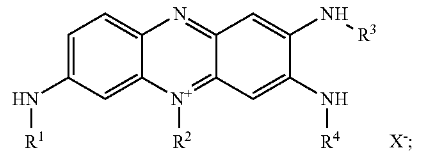

where X represents Cl, Br, OH, F, I, $BF_4$ or $PF_6$ or trifluoromethanesulfate, and where independently of each other, R1 and R2 are either a linear or branched, saturated or unsaturated, cyclic or non-cyclic C1-C18 alkyl, optionally substituted by one or more groups chosen from a hydroxyl group, an amino group, an aminoalkyl group, a C1-C5 alkoxy group, a C1-C5 alkyl, a peptide, a pyridine group, a phosphine group, a thiol, a C2 alkene, a C2 alkyne group and a halogen, or a benzyl radical optionally substituted by one or more radicals chosen from a hydroxyl group, an amino group, an aminoalkyl group, a C1-C5 alkoxy group, a C1-C5 alkyl group, and a halogen atom, or (hetero) aryl groups, optionally substituted by one or more groups chosen from a hydroxyl group, an amino group, an aminoalkyl group, a C1-C5 alkoxy group, a C1-C5 alkyl, a peptide, a pyridine group, a phosphine group, a thiol, a C2 alkene, a C2 alkyne group and a halogen, or a benzyl radical optionally substituted by one or more radicals chosen from a hydroxyl group, an amino group, an aminoalkyl group, a C1-C5 alkoxy group, a C1-C5 alkyl group, and a halogen, optionally R2 is a hydrogen atom, and independently of each other, R3 and R4 are hydrogen H or correspond to R1 or R2 mentioned above, or R3 and R4 are either or both a carbonyl functional group forming amide functions including peptides or not, or a salt or solvate thereof, or a protonated form thereof.

Compounds according to the invention that are advantageous are the following:

TABLE 1

| Compound formula | Where R1 is | Where R2 is | Where R3 is | Where R4 is |
|---|---|---|---|---|
| 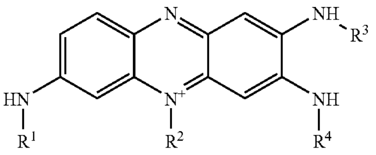 | octyl | octyl | octyl | H |
| | octyl | octyl | H | H |
| | octyl | octyl | tert-butyl | H |
| | tert-butyl | tert-butyl | tert-butyl | H |
| | nonyl | nonyl | nonyl | H |
| | nonyl | nonyl | H | H |
| | nonyl | nonyl | tert-butyl | H |
| | decyl | decyl | decyl | H |
| | decyl | decyl | H | H |
| | decyl | decyl | tert-butyl | H |
| | octyl | H | octyl | H |
| | octyl | H | H | H |
| | octyl | H | tert-butyl | H |
| | tert-butyl | H | tert-butyl | H |
| | nonyl | H | nonyl | H |
| | nonyl | H | H | H |
| | nonyl | H | tert-butyl | H |
| | decyl | H | decyl | H |
| | decyl | H | H | H |
| | decyl | H | tert-butyl | H |
| 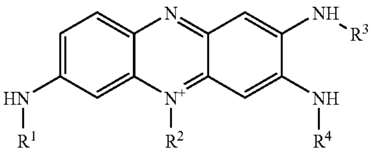 | octyl | octyl | octyl | $C_1$-$C_{18}$ |
| | octyl | octyl | H | $C_1$-$C_{18}$ |
| | octyl | octyl | tert-butyl | $C_1$-$C_{18}$ |
| | tert-butyl | tert-butyl | tert-butyl | $C_1$-$C_{18}$ |
| | nonyl | nonyl | nonyl | $C_1$-$C_{18}$ |
| | nonyl | nonyl | H | $C_1$-$C_{18}$ |
| | nonyl | nonyl | tert-butyl | $C_1$-$C_{18}$ |
| | decyl | decyl | decyl | $C_1$-$C_{18}$ |
| | decyl | decyl | H | $C_1$-$C_{18}$ |
| | decyl | decyl | tert-butyl | $C_1$-$C_{18}$ |
| | octyl | H | octyl | $C_1$-$C_{18}$ |
| | octyl | H | H | $C_1$-$C_{18}$ |
| | octyl | H | tert-butyl | $C_1$-$C_{18}$ |
| | tert-butyl | H | tert-butyl | $C_1$-$C_{18}$ |
| | nonyl | H | nonyl | $C_1$-$C_{18}$ |
| | nonyl | H | H | $C_1$-$C_{18}$ |
| | nonyl | H | tert-butyl | $C_1$-$C_{18}$ |
| | decyl | H | decyl | $C_1$-$C_{18}$ |
| | decyl | H | H | $C_1$-$C_{18}$ |
| | decyl | H | tert-butyl | $C_1$-$C_{18}$ |
| 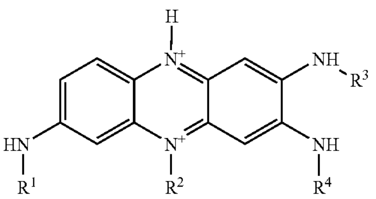 | octyl | octyl | octyl | H |
| | octyl | octyl | H | H |
| | octyl | octyl | tert-butyl | H |
| | tert-butyl | tert-butyl | tert-butyl | H |
| | nonyl | nonyl | nonyl | H |
| | nonyl | nonyl | H | H |
| | nonyl | nonyl | tert-butyl | H |
| | decyl | decyl | decyl | H |
| | decyl | decyl | H | H |
| | decyl | decyl | tert-butyl | H |
| | octyl | H | octyl | H |
| | octyl | H | H | H |
| | octyl | H | tert-butyl | H |
| | tert-butyl | H | tert-butyl | H |
| | nonyl | H | nonyl | H |
| | nonyl | H | H | H |
| | nonyl | H | tert-butyl | H |
| | decyl | H | decyl | H |
| | decyl | H | H | H |
| | decyl | H | tert-butyl | H |

TABLE 1-continued

| Compound formula | Where R1 is | Where R2 is | Where R3 is | Where R4 is |
|---|---|---|---|---|
| 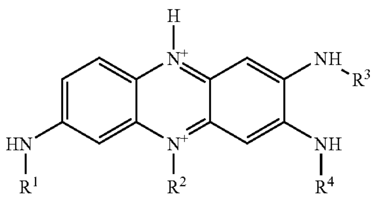 | octyl | octyl | octyl | $C_1$-$C_{18}$ |
| | octyl | octyl | H | $C_1$-$C_{18}$ |
| | octyl | octyl | tert-butyl | $C_1$-$C_{18}$ |
| | tert-butyl | tert-butyl | tert-butyl | $C_1$-$C_{18}$ |
| | nonyl | nonyl | nonyl | $C_1$-$C_{18}$ |
| | nonyl | nonyl | H | $C_1$-$C_{18}$ |
| | nonyl | nonyl | tert-butyl | $C_1$-$C_{18}$ |
| | decyl | decyl | decyl | $C_1$-$C_{18}$ |
| | decyl | decyl | H | $C_1$-$C_{18}$ |
| | decyl | decyl | tert-butyl | $C_1$-$C_{18}$ |
| | octyl | H | octyl | $C_1$-$C_{18}$ |
| | octyl | H | H | $C_1$-$C_{18}$ |
| | octyl | H | tert-butyl | $C_1$-$C_{18}$ |
| | tert-butyl | H | tert-butyl | $C_1$-$C_{18}$ |
| | nonyl | H | nonyl | $C_1$-$C_{18}$ |
| | nonyl | H | H | $C_1$-$C_{18}$ |
| | nonyl | H | tert-butyl | $C_1$-$C_{18}$ |
| | decyl | H | decyl | $C_1$-$C_{18}$ |
| | decyl | H | H | $C_1$-$C_{18}$ |
| | decyl | H | tert-butyl | $C_1$-$C_{18}$ |
| 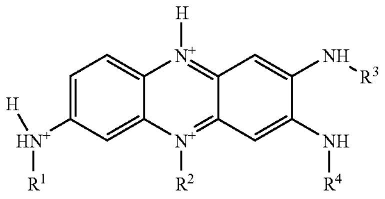 | octyl | octyl | octyl | H |
| | octyl | octyl | H | H |
| | octyl | octyl | tert-butyl | H |
| | tert-butyl | tert-butyl | tert-butyl | H |
| | nonyl | nonyl | nonyl | H |
| | nonyl | nonyl | H | H |
| | nonyl | nonyl | tert-butyl | H |
| | decyl | decyl | decyl | H |
| | decyl | decyl | H | H |
| | decyl | decyl | tert-butyl | H |
| | octyl | H | octyl | H |
| | octyl | H | H | H |
| | octyl | H | tert-butyl | H |
| | tert-butyl | H | tert-butyl | H |
| | nonyl | H | nonyl | H |
| | nonyl | H | H | H |
| | nonyl | H | tert-butyl | H |
| | decyl | H | decyl | H |
| | decyl | H | H | H |
| | decyl | H | tert-butyl | H |
| 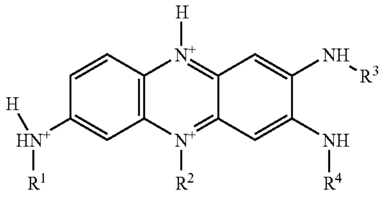 | octyl | octyl | octyl | $C_1$-$C_{18}$ |
| | octyl | octyl | H | $C_1$-$C_{18}$ |
| | octyl | octyl | tert-butyl | $C_1$-$C_{18}$ |
| | tert-butyl | tert-butyl | tert-butyl | $C_1$-$C_{18}$ |
| | nonyl | nonyl | nonyl | $C_1$-$C_{18}$ |
| | nonyl | nonyl | H | $C_1$-$C_{18}$ |
| | nonyl | nonyl | tert-butyl | $C_1$-$C_{18}$ |
| | decyl | decyl | decyl | $C_1$-$C_{18}$ |
| | decyl | decyl | H | $C_1$-$C_{18}$ |
| | decyl | decyl | tert-butyl | $C_1$-$C_{18}$ |
| | octyl | H | octyl | $C_1$-$C_{18}$ |
| | octyl | H | H | $C_1$-$C_{18}$ |
| | octyl | H | tert-butyl | $C_1$-$C_{18}$ |
| | tert-butyl | H | tert-butyl | $C_1$-$C_{18}$ |
| | nonyl | H | nonyl | $C_1$-$C_{18}$ |
| | nonyl | H | H | $C_1$-$C_{18}$ |
| | nonyl | H | tert-butyl | $C_1$-$C_{18}$ |
| | decyl | H | decyl | $C_1$-$C_{18}$ |
| | decyl | H | H | $C_1$-$C_{18}$ |
| | decyl | H | tert-butyl | $C_1$-$C_{18}$ |

TABLE 1-continued

| Compound formula | Where R1 is | Where R2 is | Where R3 is | Where R4 is |
|---|---|---|---|---|
| 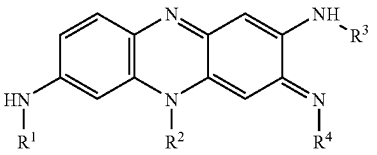 | octyl | octyl | octyl | H |
| | octyl | octyl | H | H |
| | octyl | octyl | tert-butyl | H |
| | tert-butyl | tert-butyl | tert-butyl | H |
| | nonyl | nonyl | nonyl | H |
| | nonyl | nonyl | H | H |
| | nonyl | nonyl | tert-butyl | H |
| | decyl | decyl | decyl | H |
| | decyl | decyl | H | H |
| | decyl | decyl | tert-butyl | H |
| | octyl | H | octyl | H |
| | octyl | H | H | H |
| | octyl | H | tert-butyl | H |
| | tert-butyl | H | tert-butyl | H |
| | nonyl | H | nonyl | H |
| | nonyl | H | H | H |
| | nonyl | H | tert-butyl | H |
| | decyl | H | decyl | H |
| | decyl | H | H | H |
| | decyl | H | tert-butyl | H |
| 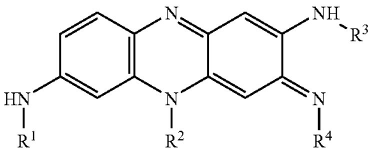 | octyl | octyl | octyl | $C_1$-$C_{18}$ |
| | octyl | octyl | H | $C_1$-$C_{18}$ |
| | octyl | octyl | tert-butyl | $C_1$-$C_{18}$ |
| | tert-butyl | tert-butyl | tert-butyl | $C_1$-$C_{18}$ |
| | nonyl | nonyl | nonyl | $C_1$-$C_{18}$ |
| | nonyl | nonyl | H | $C_1$-$C_{18}$ |
| | nonyl | nonyl | tert-butyl | $C_1$-$C_{18}$ |
| | decyl | decyl | decyl | $C_1$-$C_{18}$ |
| | decyl | decyl | H | $C_1$-$C_{18}$ |
| | decyl | decyl | tert-butyl | $C_1$-$C_{18}$ |
| | octyl | H | octyl | $C_1$-$C_{18}$ |
| | octyl | H | H | $C_1$-$C_{18}$ |
| | octyl | H | tert-butyl | $C_1$-$C_{18}$ |
| | tert-butyl | H | tert-butyl | $C_1$-$C_{18}$ |
| | nonyl | H | nonyl | $C_1$-$C_{18}$ |
| | nonyl | H | H | $C_1$-$C_{18}$ |
| | nonyl | H | tert-butyl | $C_1$-$C_{18}$ |
| | decyl | H | decyl | $C_1$-$C_{18}$ |
| | decyl | H | H | $C_1$-$C_{18}$ |
| | decyl | H | tert-butyl | $C_1$-$C_{18}$ |

More advantageously, the invention relates to the aforementioned compound, said compound having the following formula II, III or IV:

[Chem. 5]

(II)

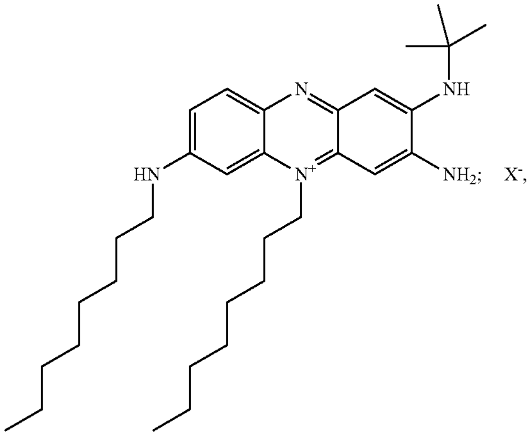

-continued

[Chem. 6]

(III)

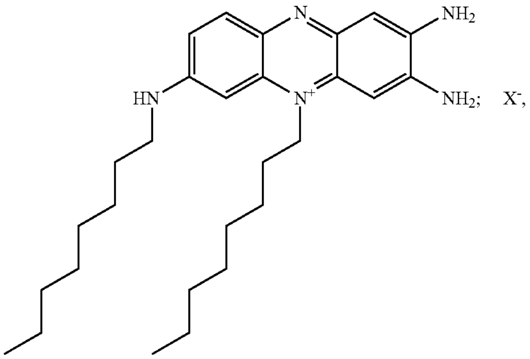

-continued

[Chem. 7]

(IV)

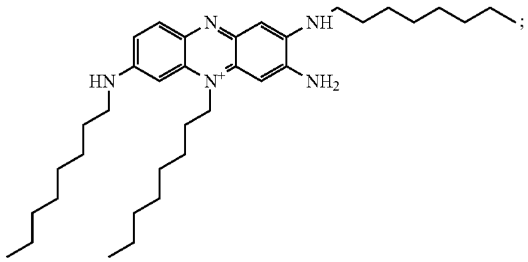

; X⁻, where X represents Cl, Br, OH, F or I.

The invention further relates to a pharmaceutical composition comprising, as active substance, a compound as defined above, in association with a pharmaceutically acceptable vehicle.

The invention relates to a compound as mentioned above, for use thereof as a drug.

According to the present invention, a pharmaceutically acceptable derivative comprises, but is not limited to, pharmaceutically acceptable salts, esters, salts of such esters, or any other adduct or derivative that, upon administration to a patient in need, is able to provide, directly or indirectly, a compound as described above, or a metabolite or residue thereof, e.g. a prodrug.

The compounds according to the invention may also be vectorized, in particular via R4, by grafting natural ligands specifically recognized by cancer cells. These biomolecules may be steroids, sugars (glucose and derivatives), amines, amino acids or peptides.

As mentioned above, “pharmaceutically acceptable vehicle” means one or more solvents, diluents, or another liquid vehicle, dispersing or suspending auxiliaries, surfactants, isotonic agents, thickening or emulsifying agents, preservatives, solid binders, lubricants and the like, depending on the particular dosage form desired. Except to the extent that a conventional carrier is incompatible with the compounds of the invention, for example by producing any adverse biological effect or otherwise interacting in a detrimental manner with any other component(s) of the aforementioned pharmaceutical composition, the use of any known carrier is envisaged within the scope of the present invention.

Some examples of materials that can serve as pharmaceutically acceptable carriers are, without limitation, sugars such as lactose, glucose, and sucrose; starches such as corn starch and potato starch; cellulose and derivatives thereof such as sodium carboxymethylcellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline solution; Ringer’s solution; ethyl alcohol and phosphate buffer solutions, and other non-toxic compatible lubricants such as sodium lauryl sulfate and magnesium stearate, as well as coloring agents, releasing agents, coating agents, sweeteners, flavoring and perfuming agents.

Preservatives and antioxidants may also be present in the composition, depending on the formulator’s judgment.

A compound according to the invention is preferably formulated in unit dosage form for ease of administration and uniformity of dosage. It is understood, however, that the total daily usage of the compounds and compositions of the present invention will be decided by the attending physician as part of the medical evaluation. The specific therapeutically effective dose level for any particular patient or organism will depend on a variety of factors comprising the disorder being treated and the severity of the disorder; the activity of the specific compound employed; the specific composition used; the age, body weight, general health, sex and diet of the patient; the time of administration, route of administration and rate of excretion of the specific compound employed; the duration of treatment; drugs used in combination or coinciding with the specific compound employed; and similar factors well known in the medical arts.

Furthermore, after formulation with an appropriate pharmaceutically acceptable excipient or vehicle in a desired dosage, the pharmaceutical compositions according to the invention may be administered to humans and other animals by the oral, rectal, parenteral, intracismal, intravaginal, intraperitoneal, dermal (e.g. by powders, ointments or drops) or buccal routes, as an oral or nasal spray, or the like depending on the severity of the disease or cancer being treated.

The active compounds according to the invention may also be in microencapsulated form, optionally with one or more excipients as noted above.

It is also appreciated that the compounds and pharmaceutical compositions of the present invention may be used in combination therapies, i.e., the compounds and pharmaceutical compositions may be administered simultaneously with, before, or after one or more other desired medical therapeutic agents or procedures.

Advantageously, the compound according to the invention has coloring properties, and may be used as a dye. Such dyes are in particular red in color, and are capable of coloring (or pigmenting) plant or animal fibers.

Due to their fluorescent properties, the compounds according to the invention may also be used as fluorescent “dyes,” in particular for labeling biological molecules or cellular organelles.

In another aspect, the invention relates to a compound as defined previously, for use thereof in the context of the treatment of pathologies by photodynamic therapy. In particular, the pathologies that may be treated with the compound according to the invention, using photodynamic therapy, are tumors (solid or hematopoietic) and keratoses.

Once a cancer is diagnosed, different methods are available to practitioners to treat the disease. These different techniques may be combined and the choice of treatment depends on the type of cancer and the stage at which it was discovered:

- surgery is traditionally used to remove the primary tumor and allows a large number of early cancers to be cured. It is now the most effective method for small tumor foci without metastasis. However, eliminating all cancer cells and preventing their spread during surgery can be difficult.
- radiotherapy, based on the action of ionizing radiation (X, α, β- or γ), is used to treat tumors, but poses the problem of the toxicity of ionizing radiation on surrounding healthy tissue.
- chemotherapy is the treatment of cancer with drugs that destroy cancer cells and prevent them from multiplying. There are many different drugs, with the choice of treatment depending on the type of cancer. However, they are not yet specific enough, since they do not yet differentiate between healthy cells and cancerous cells, thus causing many side effects.

photodynamic therapy (PDT) consists in bringing pathological tissue into contact with a photo-activatable molecule (called photo-sensitizer), then photo-activating the molecule with light in order to produce singlet oxygen, which is very toxic, which will locally destroy the cancerous lesion. The major advantage of PDT is its selectivity. Indeed, the light used alone is not harmful, and the photosensitizer without light is not toxic. To induce the reaction, a joint action of light, photosensitizer and oxygen is required. Thus, by optimizing the concentration of the photosensitizer and the dose of light (power of the laser), it is possible to selectively destroy cells.

On the therapeutic level, conventional treatments have an imperfect selectivity with respect to tumor cells. One of the reasons is that scientists have long favored the race for the $IC_{50}$ (concentration of product necessary to kill 50% of a population of cells) rather than the search for specificity. They cause side effects, sometimes severe, which limit the doses at which they can be administered.

Clinical oncology therefore calls for the joint development of new, more sensitive and more effective diagnostic methods, as well as new, more effective, better tolerated, but also better understood therapies.

Based on this need, the inventors have taken advantage of the low toxicity properties of the compounds according to the invention and their ability to produce singlet oxygen under light excitation in order to propose a photodynamic therapy.

The inventors thus propose a photodynamic therapy using the aforementioned compounds, or:

With one photon ($\lambda_{irrad.}$=514 nm), where the desired targets are surface tumors (melanoma, bladder, esophagus and bronchi) because the excitation wavelength is in the green. Although far-red (652 nm) or near-infrared (760 nm) excitation is preferred, studies have shown that for specific cases, excitation with green light is less toxic and more effective than excitation by red light. For example, in a study performed with Photofrin, on human mesothelioma xenografts in nude mice, photodynamic therapy performed with 514 nm light was shown to induce tumor-level effects, similar to those obtained with 630 nm excitation, with a decrease in normal tissue damage. Green light prevents deep tissue damage, thus reducing the risk of perforation. Since then, many studies on cells in culture or on laboratory animals have confirmed this.

With two photons ($\lambda_{irrad.}$=810 nm), the desired targets are deeper tumors (breast cancer, prostate cancer, retinoblastoma) because the excitation of the molecule with a laser in the far red or the near infrared allows deeper tissue penetration (zone of biological transparency).

Advantageously, the invention relates to a method for treating pathologies, in particular for treating tumors, by photodynamic therapy, comprising a step of administering an effective dose of compound as defined above to individuals in need, and exposure to a light beam having a wavelength varying from 450 to 850 nm.

Advantageously, the above-mentioned method is a method for treating pathologies, in particular for treating tumors, by one-photon photodynamic therapy, comprising a step of administering an effective dose of compound as defined above to individuals in need, and exposure to a light beam having a wavelength varying from 450 to 550 nm.

In the invention, "wavelength varying from 450 to 550 nm" means a wavelength of 450 nm, 451 nm, 452 nm, 453 nm, 454 nm, 455 nm, 456 nm, 457 nm, 458 nm, 459 nm, 460 nm, 461 nm, 462 nm, 463 nm, 464 nm, 465 nm, 466 nm, 467 nm, 468 nm, 469 nm, 470 nm, 471 nm, 472 nm, 473 nm, 474 nm, 475 nm, 476 nm, 477 nm, 478 nm, 479 nm, 480 nm, 481 nm, 482 nm, 483 nm, 484 nm, 485 nm, 486 nm, 487 nm, 488 nm, 489 nm, 490 nm, 491 nm, 492 nm, 493 nm, 494 nm, 495 nm, 496 nm, 497 nm, 498 nm, 499 nm, 500 nm, 501 nm, 502 nm, 503 nm, 504 nm, 505 nm, 506 nm, 507 nm, 508 nm, 509 nm, 510 nm, 511 nm, 512 nm, 513 nm, 514 nm, 515 nm, 516 nm, 517 nm, 518 nm, 519 nm, 520 nm, 521 nm, 522 nm, 523 nm, 524 nm, 525 nm, 526 nm, 527 nm, 528 nm, 529 nm, 530 nm, 531 nm, 532 nm, 533 nm, 534 nm, 535 nm, 536 nm, 537 nm, 538 nm, 539 nm, 540 nm, 541 nm, 542 nm, 543 nm, 544 nm, 545 nm, 546 nm, 547 nm, 548 nm, 549 nm or 550 nm.

Advantageously, the above-mentioned method is a method for treating pathologies, in particular for treating tumors, by two-photon photodynamic therapy, comprising a step of administering an effective dose of compound as defined above to individuals in need, and exposure to a light beam having a wavelength varying from 750 to 850 nm.

In the invention, "wavelength varying from 750 to 850 nm" means a wavelength of 750 nm, 751 nm, 752 nm, 753 nm, 754 nm, 755 nm, 756 nm, 757 nm, 758 nm, 759 nm, 760 nm, 761 nm, 762 nm, 763 nm, 764 nm, 765 nm, 766 nm, 767 nm, 768 nm, 769 nm, 770 nm, 771 nm, 772 nm, 773 nm, 774 nm, 775 nm, 776 nm, 777 nm, 778 nm, 779 nm, 780 nm, 781 nm, 782 nm, 783 nm, 784 nm, 785 nm, 786 nm, 787 nm, 788 nm, 789 nm, 790 nm, 791 nm, 792 nm, 793 nm, 794 nm, 795 nm, 796 nm, 797 nm, 798 nm, 799 nm, 500 nm, 501 nm, 502 nm, 503 nm, 504 nm, 505 nm, 506 nm, 507 nm, 508 nm, 509 nm, 510 nm, 511 nm, 512 nm, 513 nm, 514 nm, 515 nm, 516 nm, 517 nm, 518 nm, 519 nm, 520 nm, 521 nm, 522 nm, 523 nm, 524 nm, 525 nm, 526 nm, 527 nm, 528 nm, 529 nm, 530 nm, 531 nm, 532 nm, 533 nm, 534 nm, 535 nm, 536 nm, 537 nm, 538 nm, 539 nm, 540 nm, 541 nm, 542 nm, 543 nm, 544 nm, 545 nm, 546 nm, 847 nm, 848 nm, 849 nm or 850 nm.

In any of the aforementioned methods, it is advantageous to administer a compound according to the invention at a dose varying from 2 nmol·L$^{-1}$ (or nM) to 1 μmol·L$^{-1}$ (or 1000 nmol·L$^{-1}$), in particular from 2 nmol·L$^{-1}$ (or nM) to 1 μmol·L; 1 per kg for oral administration. Thus, for an individual weighing 70 kg on average, the dose administered will be from 140 nM to 70 μM. In the context of targeted administration (by injection directly into the tumor for example), the dose will be directly that described above without the mass multiplier coefficient in kg.

In the invention, "a dose varying from 2 nmol·L$^{-1}$ to 1 μmol·L$^{-1}$" means a dose of 2 nmol·L$^{-1}$, 3 nmol·L$^{-1}$, 4 nmol·L$^{-1}$, 5 nmol·L$^{-1}$, 6 nmol·L$^{-1}$, 7 nmol·L$^{-1}$, 8 nmol·L$^{-1}$, 9 nmol·L$^{-1}$, 10 nmol·L$^{-1}$, 15 nmol·L$^{-1}$, 20 nmol·L$^{-1}$, 25 nmol·L$^{-1}$, 30 nmol·L$^{-1}$, 35 nmol·L$^{-1}$, 40 nmol·L$^{-1}$, 45 nmol·L$^{-1}$, 50 nmol·L$^{-1}$, 55 nmol·L$^{-1}$, 60 nmol·L$^{-1}$, 65 nmol·L$^{-1}$, 70 nmol·L$^{-1}$, 75 nmol·L$^{-1}$, 80 nmol·L$^{-1}$, 85 nmol·L$^{-1}$, 90 nmol·L$^{-1}$, 95 nmol·L$^{-1}$, 100 nmol·L$^{-1}$, 105 nmol·L$^{-1}$, 110 nmol·L$^{-1}$, 115 nmol·L$^{-1}$, 120 nmol·L$^{-1}$, 125 nmol·L$^{-1}$, 130 nmol·L$^{-1}$, 135 nmol·L$^{-1}$, 140 nmol·L$^{-1}$, 145 nmol·L$^{-1}$, 150 nmol·L$^{-1}$, 155 nmol·L$^{-1}$, 160 nmol·L$^{-1}$, 165 nmol·L$^{-1}$, 170 nmol·L$^{-1}$, 175 nmol·L$^{-1}$, 180 nmol·L$^{-1}$, 185 nmol·L$^{-1}$, 190 nmol·L$^{-1}$, 195 nmol·L$^{-1}$, 200 nmol·L$^{-1}$, 205 nmol·L$^{-1}$, 210 nmol·L$^{-1}$, 215 nmol·L$^{-1}$, 220 nmol·L$^{-1}$, 225 nmol·L$^{-1}$, 230 nmol·L$^{-1}$, 235 nmol·L$^{-1}$, 240 nmol·L$^{-1}$, 245 nmol·L$^{-1}$, 250 nmol·L$^{-1}$, 255 nmol·L$^{-1}$, 260 nmol·L$^{-1}$, 265 nmol·L$^{-1}$, 270 nmol·L$^{-1}$, 275 nmol·L$^{-1}$, 280 nmol·L$^{-1}$, 285 nmol·$L^{-1}$, 290 nmol·$L^{-1}$, 295 nmol·$L^{-1}$, 300 nmol·$L^{-1}$, 305 nmol·$L^{-1}$, 310 nmol·$L^{-1}$, 315 nmol·$L^{-1}$, 320 nmol·$L^{-1}$, 325 nmol·$L^{-1}$, 330 nmol·$L^{-1}$, 335 nmol·$L^{-1}$, 340 nmol·$L^{-1}$, 345 nmol·$L^{-1}$, 350 nmol·$L^{-1}$, 355 nmol·$L^{-1}$, 360 nmol·$L^{-1}$, 365 nmol·$L^{-1}$, 370 nmol·$L^{-1}$, 375 nmol·$L^{-1}$, 380 nmol·$L^{-1}$, 385 nmol·$L^{-1}$, 390 nmol·$L^{-1}$, 395 nmol·$L^{-1}$, 400 nmol·$L^{-1}$, 405 nmol·$L^{-1}$, 410 nmol·$L^{-1}$, 415 nmol·$L^{-1}$, 420 nmol·$L^{-1}$, 425 nmol·$L^{-1}$, 430 nmol·$L^{-1}$, 435 nmol·$L^{-1}$, 440 nmol·$L^{-1}$, 445 nmol·$L^{-1}$, 450 nmol·$L^{-1}$, 455 nmol·$L^{-1}$, 460 nmol·$L^{-1}$, 465 nmol·$L^{-1}$, 470 nmol·$L^{-1}$, 475 nmol·$L^{-1}$, 480 nmol·$L^{-1}$, 485 nmol·$L^{-1}$, 490 nmol·$L^{-1}$, 495 nmol·$L^{-1}$, 500 nmol·$L^{-1}$, 525 nmol·$L^{-1}$, 550 nmol·$L^{-1}$, 575 nmol·$L^{-1}$, 600 nmol·$L^{-1}$, 625 nmol·$L^{-1}$, 650 nmol·$L^{-1}$, 675 nmol·$L^{-1}$, 700 nmol·$L^{-1}$, 725 nmol·$L^{-1}$, 750 nmol·$L^{-1}$, 775 nmol·$L^{-1}$, 800 nmol·$L^{-1}$, 825 nmol·$L^{-1}$, 850 nmol·$L^{-1}$, 875 nmol·$L^{-1}$, 900 nmol·$L^{-1}$, 925 nmol·$L^{-1}$, 950 nmol·$L^{-1}$, 975 nmol·$L^{-1}$ or 1000 nmol·$L^{-1}$.

Photodynamic therapy (PDT) has been used for many years in dermatology. Its theoretical principle is based on the use of a harmless molecule, accumulating preferentially in the cells to be treated. This molecule is transformed into a cytotoxic molecule after light excitation. The specificity of the treatment comes on the one hand from the pharmacokinetics of the molecule (diffusion, absorption and cellular metabolism), and on the other hand from the physics of the luminous flux.

Antitumor photodynamic therapy is therefore based on the combination of photosensitizing (Ps) molecules capable of concentrating in tumor cells, and focused light of the appropriate wavelength (Ps dependent). The combination of these two factors will allow tumor tissues to be specifically targeted and destroyed. This method still has a major drawback: only cancers accessible to light can be treated (red light, for example, only penetrates about 1 cm into living tissue).

The action of light (at a carefully selected wavelength) on the sensitizer will lead to the formation of singlet oxygen 102 (short-lived of about 0.01 to 0.004 μs), a molecule that is very reactive toward cellular components and therefore very toxic. The photosensitizer is injected intravenously; this will concentrate more or less selectively in the tumor tissue, the irradiation of which by laser light with a wavelength appropriate to the dye used leads to necrosis or apoptosis of the cancer cells.

The inventors have made the surprising observation that the compounds according to the invention, once activated at specific wavelengths, are capable of producing reactive oxygenated species in the form of singlet oxygen with a quantum yield DA of about 0.1. This low efficiency is expected, since the vast majority of absorbed photons (76%) are converted into light.

Surprisingly, however, the inventors have noticed that this yield is largely sufficient to lead in vitro to the destruction of 98% of the tumor cells at very low concentrations of about 100 nM.

The invention also relates to a compound as defined previously, for use thereof in the context of diagnosing pathologies, in particular cancers.

Fluorescence imaging is one of the most powerful techniques for observing dynamic intracellular processes in living cells. Access to new adaptable fluorescent probes is of major importance because only very few biomolecules can currently be visualized due to inherent limitations in the structure of the probes used to date.

The imaging proposed, or the use of the compounds according to the invention, is based on conventional one-photon or two-photon fluorescence, as described above.

The invention further relates to a method of in vivo fluorescence imaging, comprising a step of administering an effective dose of compound as defined above to individuals in need, and exposure to a light beam having a wavelength varying from 450 to 850 nm, and a step of detection by appropriate means of fluorescent cells, tissues or cell organelles.

The invention further relates to a method of in vivo fluorescence imaging, comprising a step of administering an effective dose of compound as defined above to individuals in need, and exposure to a light beam having a wavelength varying from 450 to 550 nm, and a step of detection by appropriate one-photon fluorescence detection means of fluorescent cells, tissues or cell organelles.

The invention further relates to a method of in vivo fluorescence imaging, comprising a step of administering an effective dose of compound as defined above to individuals in need, and exposure to a light beam having a wavelength varying from 750 to 850 nm, and a step of detection by appropriate two-photon fluorescence detection means of fluorescent cells, tissues or cell organelles.

The invention also relates to the use of an aforementioned compound, for the in vitro or ex vivo visualization of living cells, of cytoplasmic organelles (mitochondria, endoplasmic reticulum, Golgi apparatus, vesicles, nucleus, etc.) or of tissues, by one- or two-photon fluorescence microscopy, said compound being used in particular at a concentration varying from 2 to 500 nmol·$L^{-1}$.

The invention also relates to a method, in particular in vitro, for visualizing living cells, cytoplasmic organelles (mitochondria, endoplasmic reticulum, Golgi apparatus, vesicles, nucleus, etc.) or tissues, by fluorescence microscopy, comprising:

- a step of bringing living cells, cytoplasmic organelles or tissues, previously taken from an individual or an animal, into contact with a compound mentioned above, at a concentration of 2 to 500 nmol·$L^{-1}$.
- a step of exposure to a light beam having a wavelength varying from 450 to 850 nm, and
- a step of detection by appropriate one- or two-photon fluorescence detection means of the fluorescent cells, tissues or organelles.

The invention also relates to a method, in particular in vitro, for eradicating cells comprising a step of using a light source emitting one or two photons to expose cells treated with a compound according to one of claims 1 to 4, said compound being used at a concentration varying from 1 to 1000 nmol·$L^{-1}$.

The invention also relates to the use of a compound mentioned above for the eradication, in particular in vitro, of cells.

Another aspect of the invention relates to a method of diagnosis, in particular in vitro, of a pathology involving a deregulation of the expression or the activity of one or more peptidases, amidases or both, from a biological sample from individuals affected by said pathology, comprising:

- a step of bringing said biological sample into contact with a compound as defined in one of claims 1 to 3, where R4 is a functional group inhibiting the fluorescent properties of said compound,
- a step of fluorescence detection after exposure to a light beam having a wavelength varying from 450 to 850 nm.

The inventors have made the surprising observation that certain R4 groups, in particular (Carbonyl of the C(O-alkyl or C(O)-aryl type), drastically modify the fluorescence properties of the compounds according to the invention. However, once these groups are cleaved, by breaking the amide function, the compounds recover their initial fluorescence capacities.

Thus, the compounds of the invention where R4 is a group strongly impacting fluorescence may serve as a diagnostic probe for detecting abnormal peptidase or amidase activity within cells, a deregulation that is correlated with a pathology.

Therefore, if the cell is healthy, no fluorescence will be emitted after excitation, or fluorescence at a certain level FO will be measurable. If, however, the cell is a cell with increased peptidade/amidase activity compared to the healthy cell, or simply begins to express the peptidade/amidase that is not expressed in the healthy cell, the R4 group will be cleaved, or will be more cleaved, and a difference in fluorescence will be observed.

In the same way, if the pathological cell has a decrease in peptidade/amidase activity compared to the healthy cell, the fluorescence in the pathological cells will be weaker, or even disappear.

The invention will be better understood in the light of the following examples and drawings.

EXAMPLES

Commercial analytical-grade reagents were obtained from suppliers and used directly without further purification. The $^{1}H$ and $^{13}C$ NMR spectra are recorded in $CDCl_3$, $CD_2Cl_2$, $CD_3CN$, acetone-de and DMSO-$d_6$, determined with a Brucker AC250 spectrometer operating at 250 MHz or with a Jeol ECS400 spectrometer operating at 400 MHz. Chemical shifts are expressed in ppm and coupling constants (J) are in hertz. Separation patterns are designed in the form of s, singlet; br s, broad singlet; d, doublet; dd, doublet of doublets; t, triplet; td, triplet of doublets; qt, quintet.

The elemental and MS (mass spectrometry) analyses were carried out by the Spectropole de Marseille. ESI mass spectral analyses are recorded with a mass spectrometer 3200 QIRAP (Applied Biosystems SCIEX). High-resolution mass spectral analyses are recorded with a SYNAPT G2 HDMS mass spectrometer (Waters)

The preparative flash column chromatographies were carried out using silica gel G60 230-240 mesh (Merck).

Example 1—Syntheses of Compounds According to the Invention

1—Synthesis Method No. 1-Compound of Formula III (1a)

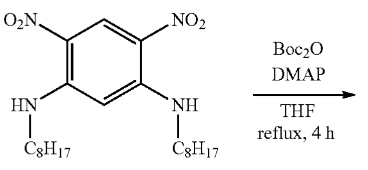

A

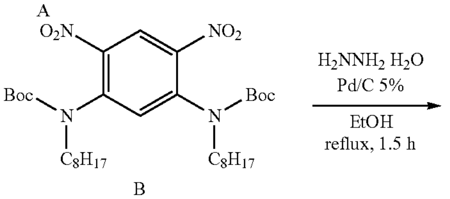

B

-continued

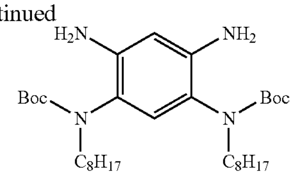

8b

Compound A: 1-Octylamine (v=830 μL, 2.05 equiv.) and N,N-diisopropylethylamine (DIPEA) (v=874 μL, 2.05 equiv.) was added to a solution of 1,5-difluoro-2,4-dinitrobenzene (DFNB) (m=500 mg, 1.00 equiv.) in ethanol (v=50 mL). The solution was heated to reflux for 1.5 h. After cooling to room temperature, the resulting solid in suspension was isolated by filtration, rinsed with EtOH and dried under vacuum to obtain compound A (m=1.04 g, quantitative yield) in an orange crystalline form.

$^{1}H$ NMR (250 MHz, $CDCl_3$): δ 9.24 (s, 1H), 8.32 (br s, 2H), 5.65 (s, 1H), 3.27 (td, $J_t$=7.0 Hz, $J_d$=5.3 Hz, 4H), 1.82-1.71 (m, 4H), 1.54-1.29 (m, 20H), 0.89 (t, J=6.8 Hz, 6H). $^{13}C$ NMR (63 MHz, $CDCl_3$): δ 148.5, 129.5, 124.0, 90.0, 43.3, 31.7, 29.2, 29.1, 28.4, 27.1, 22.6, 14.0. ESI-MS: m/z $[M+H]^+$ 423.3 (100%), $[M+Na]^+$ 445.3 (6%), $[M+K]^+$ 461.3 (4%); $[MH]^-$ 421.3 (100%). Elemental analysis for $C_{22}H_{38}N_4O_4$: calculated. C 62.53, H 9.06, N 13.26, O 15.15; found C 62.58, H 9.19, N 13.21

Compound B: $Boc_2O$ (m=1.94 g, 8.89 mmol, 3.7 equiv.) and 4-dimethylaminopyridine (DMAP) (m=50 mg, 0.41 mmol, 17 mol %) were added to a solution of compound A (m=1.03 g, 2.43 mmol, 1.0 equiv.) in THF (10 mL). The solution was refluxed for 4 h. The solvent was removed under vacuum. The crude product was purified by flash chromatography (silica F60, DCM 100) to obtain compound B (m=1.52 g, 2.44 mmol, quantitative yield) in the form of a yellow solid.

$^{1}H$ NMR (250 MHz, $CDCl_3$): δ 8.54 (s, 1H), 7.24 (s, 1H), 3.69 (m, 4H), 1.68-1.25 (m, 42H), 0.87 (t, J=6.5 Hz, 6H). $^{13}C$ NMR (63 MHz, $CDCl_3$): 152.1, 142.5, 141.0, 127.8, 122.8, 82.9, 50.9, 31.7, 29.2, 29.2, 28.7, 27.9, 26.9, 22.6, 14.0. MS: ESI-MS: m/z $[M+NH_4]^+$ 640.4 (100%), $[M+Na]^+$ 645.4 (12%), $[M+K]^+$ 661.3 (5%). Elemental analysis for $C_{32}H_{54}N_4O_8$: calculated. C 61.71, H 8.74, N 9.00, O 20.55; found C 61.68, H 8.96, N 8.82.

Compound 8b: Compound B (m=5.15 g, 8.28 mmol, 1.0 equiv.) and hydrazine monohydrate (2.3 mL, 47.1 mmol, 5.7 equiv.) were added to a suspension of Pd on carbon carbon 5% (m=180 mg, 0.085 mmol, 1% mol) in EtOH (80 mL). The mixture was heated to reflux for 1.5 h. The Pd/C was removed by filtration through Celite 545, and the solid phase was rinsed with dichloromethane (3×100 mL). The combined organic phase was washed with water (3×150 mL) and brine (100 mL), dried with anhydrous $MgSO_4$, filtered, concentrated and dried under vacuum to obtain compound 8b (m=4.43 g, 7.87 mmol, 96% yield) as a yellow solid.

$^{1}H$ NMR (250 MHz, $CDCl_3$): δ 6.55 (br s, 1H), 6.09 (s, 1H), 3.58 (br s, 6H), 3.27 (m, 2H), 1.51-1.24 (m, 42H), 0.86 (t, J=6.5 Hz, 6H). $^{13}C$ NMR (63 MHz, $CDCl_3$): 155.2, 142.7, 142.5, 129.5, 129.1, 118.9, 102.0, 79.2, 57.6, 48.4, 31.5, 29.1, 29.0, 28.0, 26.6, 22.3, 18.1, 13.8. HRMS (ESI-TOF): m/z $[M+H]^+$ for $C_{32}H_{59}N_4O_4^+$ calculated. 563.4531, found 563.4532, err.<1 ppm; m/z $[M+NH_4]^+$ for $C_{32}H_{62}N_5O_4^+$ calculated. 580.4796, found 580.4803, err. <2 ppm.

Compound 12b: TFA at 0° C. was added to a solution of compound 8b (m=303 mg, 0.538 mmol) in dichloromethane (v=5 mL), HCl (12N, v=2 mL). This mixture was stirred under argon overnight. The resulting solid in suspension was collected by filtration, rinsed with $CH_2Cl_2$ (v=20 mL), and dried under vacuum to obtain compound 12b (m=196 mg, 0.449 mmol, 84% yield) in the form of a light pink solid. This raw product was used directly without further purification.

$^1$H NMR (250 MHz, DMSO-$d_6$): δ 6.85 (br s, 1H), 6.44 (br s, 1H), 3.06 (t, $^3J_{HH}$=7.2 Hz, 4H), 1.62 (m, 4H), 1.35-1.26 (m, 20H), 0.86 (t, $^3J_{HH}$=6.8 Hz, 6H). No 13C NMR spectrum could be recorded owing to the poor stability in solution. MALDI-TOF MS: m/z $M^{+*}$ for $C_{22}H_{42}N_4^{*+}$ calculated. 362.3, found 362.3 (100%).

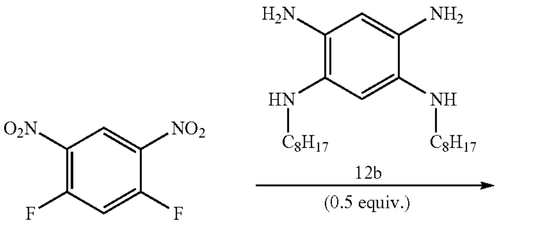

DFDNB

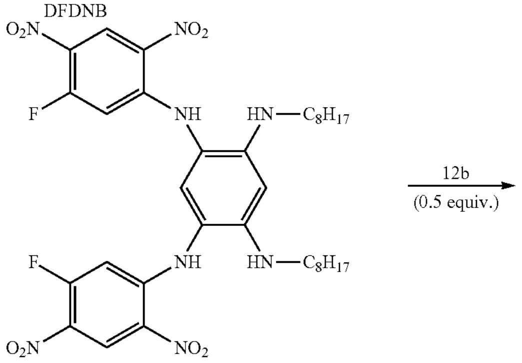

13b

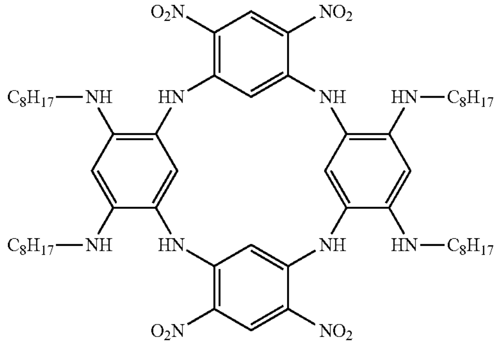

3

Compound 13b: Compound 12b (m=306 mg, 0.703 mmol, 1.0 equiv.) was added to a solution of DFDNB (m=258 mg, 1.27 mmol, 1.8 equiv.) in MeCN (v=25 mL). The flask was closed with a septum and the solution was cooled in an ice water bath and degassed. $N(iPr)_2Et$ (v=735 μL, 4.22 mmol, 6.0 equiv.) was then added dropwise using a syringe under argon. The solution was stirred at 0° C. for 2 hours, then at room temperature for an additional two hours. The solution was concentrated in vacuo, and the residue taken up with EtOH (v=30 mL) and MeCN (v=10 mL). The solid obtained in suspension was recovered by filtration, rinsed with EtOH (v=100 mL) and $Et_2O$ (v=20 mL), and dried under vacuum to obtain compound 13b in the form of an orange powder (m=365 mg, 0.499 mmol, 79% yield).

$^1$H NMR (250 MHz, $CDCl_3$): δ 9.29 (br s, 2H), 9.15 (d, $^4J_{HF}$=7.8 Hz, 2H), 6.84 (s, 1H), 6.52 (d, $^3J_{HF}$=13 Hz, 2H), 6.07 (s, 1H), 3.97 (br s, 2H), 3.19 (t, $^3J_{HH}$=7.0 Hz, 4H), 1.66-1.26 (m, 24H), 0.88 (t, $^3J_{HH}$=7.0 Hz, 6H). $^1$H NMR (250 MHz, Acetone-$d_6$): δ 9.60 (br s, 2H), 9.01 (d, $^4J_{HF}$=8.0 Hz, 2H), 7.08 (s, 1H), 6.70 (d, $^3J_{HH}$=14.3 Hz, 2H), 6.20 (s, 1H), 5.13 (br s, 2H), 3.24 (t, $^3J_{HH}$=7.0 Hz, 4H), 1.66-1.55 (m, 4H), 1.29-1.26 (m, 20H), 0.87 (t, $^3J_{HH}$=7.0 Hz, 6H). $^{13}$C NMR (63 MHz, $CDCl_3$): δ 159.9 (d, $^1J_{CF}$=267 Hz), 150.0, 149.8, 146.1, 127.9, 127.6, 127.3 (d, $^2J_{CF}$=10.1 Hz), 109.8, 103.7 (d, $^2J_{CF}$=27.7 Hz), 93.4, 43.5, 31.7, 29.28, 29.23, 29.18, 27.1, 22.6, 14.0. HRMS (ESI-TOF): m/z $[M+H]^+$ for $C_{34}H_{45}N_8O_8F_2^+$ calculated. 731.3323, found 731.3323, err. <1 ppm.

Compound 3: Compound 12b (m=115 mg, 0.263 mmol, 1.2 equiv.) was added to a solution of compound 13b (m=160 mg, 0.219 mmol, 1.0 equiv.) in anhydrous MeCN (v=30 mL). The flask was closed, degassed and $N(iPr)_2Et$ was added dropwise (m=370 μL, 2.12 mmol, 9.6 equiv.) using a syringe under argon. The mixture was stirred at room temperature for 2 h with stirring, then refluxed overnight. After concentration of the solvent under vacuum, the residue was taken up with a mixture of acetone (v=5 mL) and ethanol (v=5 mL). The resulting solid product was isolated by filtration, washed with EtOH and dried under vacuum to obtain Compound 3 (m=155.5 mg, 0.148 mmol, 68% yield) as an orange powder.

$^1$H NMR (250 MHz, $CDCl_3$): δ 9.26 (s, 2H), 8.85 (br s, 4H), 6.58 (s, 2H), 5.82 (s, 2H), 5.49 (s, 2H), 3.91 (br t, $^3J_{HH}$=5.4 Hz, 4H), 3.09-2.99 (m, 8H), 1.53-1.28 (m, 48H), 0.89 (t, $^3J_{HH}$=6.8 Hz, 12H). $^{13}$C NMR (63 MHz, $CDCl_3$): δ 149.9, 146.4, 129.2, 129.0, 125.4, 110.6, 95.7, 92.6, 43.8, 31.8, 29.49, 29.46, 29.33, 27.3, 22.7, 14.1. HRMS (ESI-TOF): m/z $[M+H]^+$ for $C_{56}H_{85}N_{12}O_8^+$ calculated. 1053.6608, found 1053.6608, err. <1 ppm.

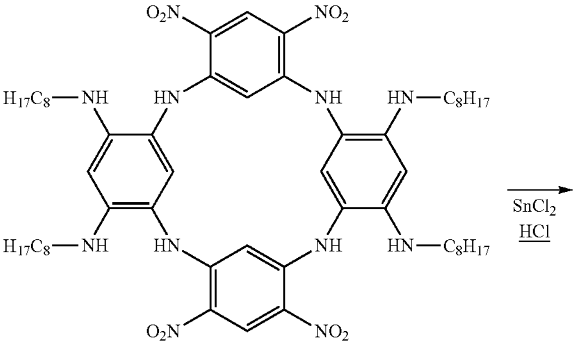

3

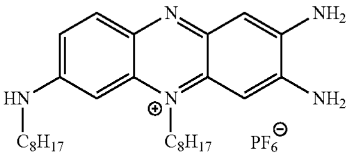

1a

Compound 1a: $SnCl_2 \cdot 2H_2O$ (343 mg, 1.52 mmol, 32 equiv.) and HCl (12M, 0.13 mL) were added to a solution of macrocycle 3 (50 mg, 0.05 mmol, 1 equiv.) in absolute ethanol (50 mL). The mixture was stirred at reflux overnight and neutralized with $NaHCO_3$ before adding ethanol (30 mL) and water (20 mL).

After evaporation of the solvent under reduced pressure, the residue was extracted with a dichloromethane/ethanol mixture (3/1, v/v). The red organic layer was washed with an aqueous solution of $HPF_6$ (1 wt. % in water, 4×150 mL) and brine (100 mL), dried with $MgSO_4$ and concentrated in vacuo to obtain compound 1a [$PF_6$] as a dark red solid (35 mg, 62% yield). 5

$^1H$ NMR (400 MHz, $CD_3CN$): δ 7.82 (d, J=9.3 Hz, 1H), 7.23 (dd, J=9.3 Hz, J=2.2 Hz, 1H), 7.18 (s, 1H), 6.99 (s, 1H), 6.55 (d, J=2.2 Hz, 1H), 6.33 (br t, J=5.2 Hz, 1H), 6.12 (br s, 2H), 4.84 (br s, 2H), 4.57 (t, J=8.2 Hz, 2H), 3.37 (td, J=6.9 Hz, J=6.0 Hz, 2H), 1.72 (quint, J=7.3 Hz, 2H), 1.61 (quint, J=7.8 Hz, 2H), 1.47-1.27 (m, 20H), 0.91-0.87 (m, 6H). HRMS (ESI-TOF): m/z $[M+NH_4]^+$ for $C_{28}H_{44}N_5^+$ calculated. 450.3591, found 450.3592, err. <1 ppm.

2—Synthesis Method No. 2-Compound of Formula IV (1c)

J=2.3 Hz, 1H), 4.52 (br s, 1H), 3.23-3.14 (m, 4H), 1.75-1.62 (m, 4H), 1.42-1.28 (m, 20H), 0.91-0.85 (m, 6H). $^{13}C$ NMR (63 MHz, $CDCl_3$): 154.4, 148.6, 129.2, 123.6, 104.7, 89.8, 43.3, 42.9, 31.8, 31.7, 29.3, 29.2, 29.1, 28.8, 27.1, 27.0, 22.6, 14.0. MS: ESI-MS: m/z $[M+H]^+$ 378.3 (100%); $[MH]^-$ 376.3 (100%), $[M+CH_3COO]^-$ 436.3 (48%). Elemental analysis for $C_{22}H_{39}N_3O_2\cdot\frac{1}{5}C_2H_5OH$: calculated. C 69.56, H 10.48, N 10.86, O 9.10; found C 69.41, H 10.39, N 10.92.

Compound 12 h: a solution of compound 4 (628 mg, 1.66 mmol, 1 equiv.) in THF (25 mL) was hydrogenated (40 bars) overnight in the presence of Pd/C (5 wt. %, 36 mg, 0.02 mmol, 1 mol %). After reducing the pressure, the solution was degassed under sonication for 5 min. 1,5-difluoro-2,4-dinitrobenzene (320 mg, 1.58 mmol, 0.95 equiv.) was added to the solution with stirring at 0° C. The solution was left at this temperature for a further 10 min and the completion of

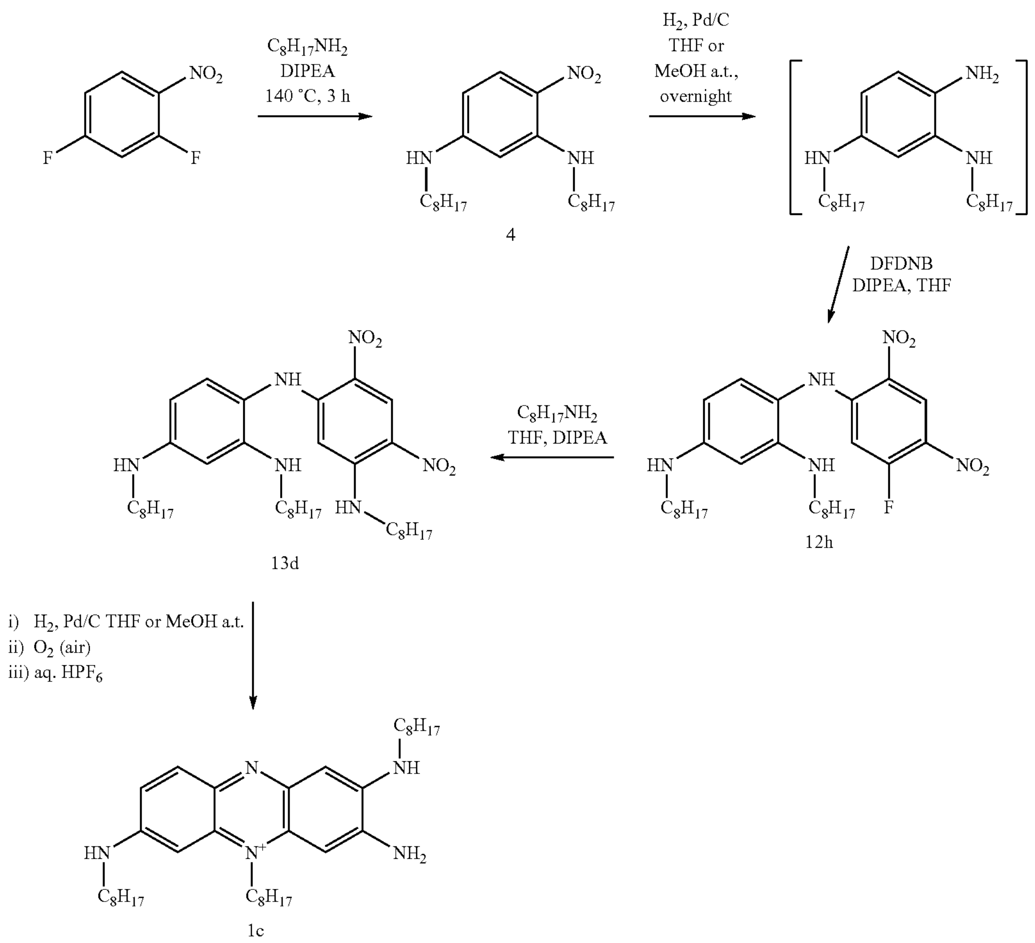

4
12h
13d
1c

Compound 4:2,4-difluoronitrobenzene (6.5 mL, 0.059 mol, 1 equiv.), 1-octylamine (40 mL, 0.243 mol, 4.1 equiv.) and DIPEA (18 mL, 0.101 mol, 1.7 equiv.) were introduced into a pressure canister, which was closed with a Teflon seal cap. The mixture was heated to 145° C. for 3 h. After cooling to room temperature, 15 mL of ethanol was added. This suspension was triturated by ultrasound. The resulting solid product in suspension was isolated by filtration, rinsed with hot water, and dried under vacuum to obtain compound 4 in the form of a yellow powder (21.6 mg, 96% yield).

$^1H$ NMR (250 MHz, $CDCl_3$): δ 8.52 (br s, 1H), 7.99 (d, J=9.3 Hz, 1H), 5.89 (dd, J=9.3 Hz, J=2.3 Hz, 1H), 5.62 (d, the reaction was monitored by TLC. Then DIPEA (301 μL, 1.66 mmol, 1 equiv.) was added to neutralize the solution. The Pd/C was removed by filtration through celite. The crude product was purified by flash chromatography on silica gel using a dichloromethane/cyclohexane mixture (1/1) as eluent to obtain compound 12 h in the form of a red solid (620 mg, 75% yield).

$^1H$ NMR (400 MHz, $CDCl_3$): δ 9.31 (s, 1H), 9.15 (d, J=7.7 Hz, 1H), 6.83 (d, J=8.4 Hz, 1H), 6.53 (d, J=13.4 Hz, 1H), 6.00 (dd, J=8.4, 2.3 Hz, 1H), 5.95 (d, J=2.1 Hz, 1H), 3.77 (s, 1H), 3.67 (s, 1H), 3.11 (td, J=14.1, 8.4 Hz, 4H), 1.65 (quintet, J=7.2 Hz, 2H), 1.56 (quintet, J=7.1 Hz, 2H), 1.36

(m, 20H), 0.89 (t, J=6.7 Hz, 3H), 0.87 (t, J=6.7 Hz, 3H). $^{13}C$ NMR (100 MHz, $CDCl_3$): δ 159.9 (d, $J_{CF}$=270.7 Hz), 150.5, 150.3, 150.2, 145.1, 128.5, 127.7, 127.7, 127.6, 126.9 (d, $J_{CF}$=10.2 Hz), 110.7, 103.9 (d, $J_{CF}$=27.4 Hz), 101.6, 95.1, 43.9, 43.4, 31.8, 31.8, 31.8, 29.5, 29.4, 29.3, 29.3, 29.3, 29.3, 29.2, 29.2, 27.2, 27.1, 22.7, 22.6, 14.1, 14.1. HRMS (ESI-TOF): m/z $[M+H]^+$ for $C_{28}H_{43}FN_5O_4^+$ calculated. 532.3294, found 532.3281, err. <2 ppm.

Compound 13d: a solution of compound 4 (628 mg, 1.66 mmol, 1 equiv.) in THF (25 mL) was hydrogenated (40 bars) overnight in the presence of Pd/C (5 wt. %, 36 mg, 1 mol %). After decreasing the pressure, the solution was degassed by sonication for 5 min, then cooled to 0° C. in an ice tray, and 1,5-difluoro-2,4-dinitrobenzene (320 mg, 1.58 mmol, 0.95 equiv.) was added to the solution with stirring. The reaction was maintained at 0° C. for 10 min. Then 1-octylamine (286 μL, 1.93 mmol, 1.1 equiv.) and DIPEA (289 μL, 1.66 mmol, 1 equiv.) were added. The mixture was stirred at room temperature for 3 days. After filtration through celite and concentration, the raw product was purified by flash chromatography on silica gel using a dichloromethane/cyclohexane mixture (50/50 to 55/45) as eluent to obtain compound 13d in the form of a red solid (498 mg, 49% yield).

TLC: $R_f$=0.27 ($SiO_2$ F60, dichloromethane/cyclohexane, 7/3). $^1H$ NMR (400 MHz, $CDCl_3$): δ 9.27 (s, 1H), 9.12 (br s, 1H), 8.21 (br t, J=4.8 Hz, 1H), 6.87 (d, J=8.3 Hz, 1H), 6.00 (dd, J=8.3, 2.2 Hz, 1H), 5.96 (d, J=2.2 Hz, 1H), 5.69 (s, 1H), 3.77 (br s, 1H), 3.68 (br s, 1H), 3.13 (t, J=7.2 Hz, 2H), 3.13-3.05 (m, 2H), 3.00 (q, J=6.1 Hz, 2H), 1.68-1.52 (m, 6H), 1.45-1.23 (m, 30H), 0.90-0.84 (m, 9H). $^{13}C$ NMR (100 MHz, $CDCl_3$): δ 149.5, 149.0, 148.4, 145.2, 129.4, 128.6, 124.8, 124.3, 112.0, 101.5, 95.2, 93.0, 44.1, 43.5, 43.1, 31.8, 31.8, 31.7, 29.6, 29.4, 29.4, 29.3, 29.2, 29.2, 29.2, 29.1, 28.2, 27.2, 27.1, 26.9, 22.6, 22.6, 22.6, 14.1, 14.1, 14.0. HRMS (ESI-TOF): m/z $[M+I]^-$ for $C_{36}H_{60}N_6O_4I^-$ calculated. 767.3726, found 767.3725, err. <2 ppm.

Compound 1c: A solution of compound 13d (200 mg, 0.31 mmol, 1 equiv.) in methanol (40 mL) was hydrogenated (40 bars) overnight in the presence of Pd/C (5 wt. %) and HCl (12M, 0.1 mL). Then the mixture was stirred in air for 24 hours. The Pd/C was removed by filtration through celite. After removal of the solvent under reduced pressure, the resulting solid was taken up with dichloromethane (80 mL), washed with a solution of aqueous $HPF_6$ (1 wt. % in water, 2×50 mL) then distilled water (50 mL) and in fine concentrate. The residue was purified by flash chromatography on standard alumina 90 using a dichloromethane/cyclohexane mixture (100/0 to 99/1) as eluent to obtain compound 1c $[PF_6^-]$ as a red solid (192 mg, 87% yield).

$^1H$ NMR (400 MHz, $CD_3CN$): δ 7.78 (d, J=9.2 Hz, 1H), 7.19 (dd, J=9.2 Hz, 1.7 Hz, 1H), 6.96 (s, 1H), 6.89 (s, 1H), 6.52 (d, J=1.7 Hz, 1H), 6.24 (br t, J=5.2 Hz, 1H), 6.18 (br s, 2H), 4.78 (br s, 1H), 4.54 (t, J=8.1 Hz, 2H), 3.34 (td, J=6.7 Hz, 6.0 Hz, 2H), 3.28 (td, J=6.7 Hz, 5.2 Hz, 2H), 1.79-1.67 (m, 4H), 1.64-1.56 (m, 2H), 1.51-1.30 (m, 30H), 0.91-0.88 (m, 9H). $^{13}C$ NMR (100 MHz, DMSO-$d_6$): δ=152.6, 150.3, 138.7, 138.3, 134.9, 132.2, 131.3, 130.2, 102.5, 92.3, 47.1, 43.1, 42.5, 31.2, 31.2, 28.8, 28.8, 28.7, 28.6, 28.0, 27.6, 26.7, 26.6, 26.2, 26.0, 22.0, 13.9, 13.9. HRMS (ESI-TOF): m/z $[M+H]^+$ for $C_{36}H_{60}N_5^+$ calculated. 562.4843, found 562.4855, err. <3 ppm.

Synthesis of Compounds where R2 is Hydrogen

PR4 Compound

Compound 12: 5-fluoro-2-nitroaniline

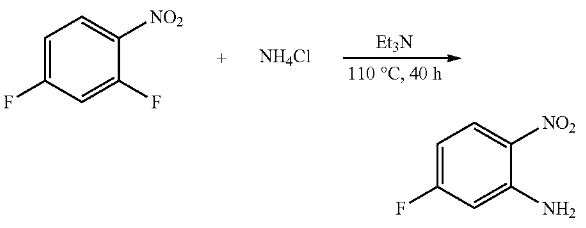

12

DFDNB (1.0 mL, 9.11 mmol, 1.0 eq), $NH_4Cl$ (975 mg, 18.2 mmol, 2.0 eq) and triethylamine (9.0 mL) were introduced in a pressure bomb. The bomb was closed with a Teflon cap. The mixture was allowed to heat up to 110° C. for 40 hrs. After cooling to room temperature, the raw product was placed in a mixture of DCM (150 mL) and water (150 mL). While stirring, 12N HCl was added dropwise until the pH of the aqueous phase reached approximately 1. The organic phase was separated and washed with water (150 mL), dried with $MgSO_4$. Additional heptane (40 mL) was added to this solution. The solvent was removed by lowering the pressure. The residues were dried under vacuum to obtain compound 12 (1.25 g, 8.01 mmol, 88% yield) as a yellow powder. $^1H$ NMR (400 MHz, $CDCl_3$): δ 8.184 (dd, J=9.6 Hz, J=5.6 Hz, 1H), 6.449-6.41 (m, 2H), 6.200 (br s, 2H) $^{13}C$ NMR (100 MHz, $CDCl_3$): δ 168.2 (d, J=260 Hz), 146.7, 146.6, 129.4 (d, J=12 Hz), 105.9 (d, J=25 Hz), 103.8 (d, J=26 Hz). MS: ESI-MS: m/z $[M+Li]^+$ 157.1 (26%), $[M+Li]^+$ 163.1 (100%); $[MH]^-$ 154.9 (100%). Elemental analysis for $C_6H_5FN_2O_2$: calculated. C 46.16, H 3.23, F 12.17, N 17.94, W 20.50; found C 46.63, H 3.15, N 17.90.

Compound 13:

4-Nitro-$N^1$-octylbenzene-1,3-diamine

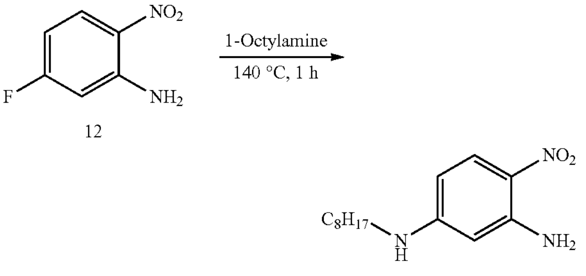

12

13

Compound 12 (808 mg, 5.18 mmol, 1.0 eq) and 1-octylamine (3.0 mL, 18.2 mmol, 3.5 eq) were introduced into a pressure bomb. The bomb was closed with a Teflon cap. The mixture was stirred at 140° C. for 1 hour. After cooling to room temperature, heptane (10 mL) was added. The resulting solid in suspension was isolated by filtration, purified by chromatography (60F silica, DCM, 100) to obtain compound 13 (1.23 g, 4.64 mmol, 90% yield) as a yellow solid.

$^1H$ NMR (250 MHz, $CDCl_3$): δ 7.96 (d, J=9.3 Hz, 1H), 5.97 (dd, J=9.3 Hz, J=2.5 Hz, 1H), 5.71 (d, J=2.5 Hz, 1H), 3.15 (t, J=7.1 Hz, 2H), 1.67 (quint, J=7.1 Hz, 2H), 1.40-1.28 (m, 10H), 0.90 (t, J=7.1 Hz, 3H). $^{13}C$ NMR (63 MHz, $CDCl_3$): δ 153.9, 147.9, 128.4, 124.2, 106.2, 94.8, 43.4, 31.7, 29.2, 29.1, 29.0, 27.0, 22.6, 14.0 MS: ESI-MS: m/z $[M+H]^+$ 266.3 (100%), $[M+Li]^+$ 272.3 (19%), $[M+Na]^+$ 288.3 (4%); $[MH]^-$ 264.1 (100%). Elemental analysis for $C_{14}H_{23}N_3O_2$: calculated. C 63.37, H 8.74, N 15.84, O 12.06; found C 63.65, H 8.83, N 15.66.

Compound 14: $N^4$-octylbenzene-1,2,4-triamine

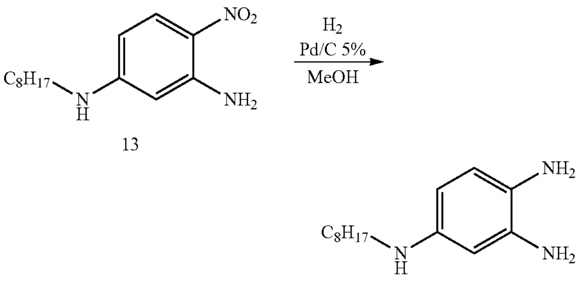

13

14

A solution of compound 13 (975 mg, 3.67 mmol) in MeOH (75 mL) was hydrogenated (40 bars) in the presence of Pd/C (5%) overnight. The Pd/C was then removed by filtration through Celite. After concentration under reduced pressure and drying under vacuum, compound 14 was obtained in the form of a deep green solid (870 mg, 3.69 mmol, quantitative yield). $^1H$ NMR (400 MHz, $CDCl_3$): δ 6.60 (d, J=8 Hz, 1H), 6.07 (d, J=2.4 Hz, 1H), 6.03 (dd, J=8 Hz, J=2.4 Hz, 1H), 3.11 (br s, 5H), 3.03 (t, J=7.2 Hz, 2H), 1.61 (quint, J=7.2 Hz, 2H), 1.38-1.28 (m, 10H), 0.90 (t, J=6.8 Hz, 3H)

$^{13}C$ NMR (100 MHz, $CDCl_3$): 143.5, 137.4, 124.8, 119.4, 104.7, 102.1, 45.1, 31.8, 29.6, 29.4, 29.3, 27.2, 22.6, 14.1. Elemental analysis for $C_{14}H_{25}N_3$: calculated. C 71.44, H 10.71, N 17.85; found C 71.23, H 10.82, N 17.88.

Compound 20: $N^1$-(2,4-dinitro-5-(octylamino)phenyl)-$N^4$-octylbenzene-1,2,4-triamine

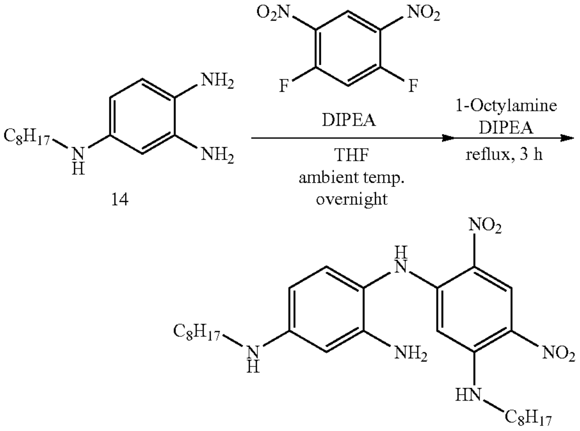

14

20

DFDNB (671.5 mg, 3.29 mmol, 0.90 eq) was added to a solution of compound 14 (860 mg, 3.65 mmol, 1.00 eq) in THF (40 mL). The flask was sealed and degassed by 3 pump-argon cycles. Degassed DIPEA (640 UL, 3.67 mmol, 1.00 eq) was added dropwise using a syringe under argon. The mixture was stirred at room temperature overnight. 1-Octylamine (604 μL, 3.65 mmol, 1.00 eq) and additional DIPEA (660 μL, 3.79 mmol, 1.04 eq) were added. The solution was heated to reflux for 3 h and cooled to room temperature. After concentration of the solvent in vacuo, the resulting solid product was isolated by filtration before the addition of EtOH (40 mL), rinsed with EtOH (6×10 mL) and dried in vacuo to obtain compound 20 (1.36 g, 2.57 mmol, 79% yield) as a yellow powder. $^1H$ NMR (400 MHz, $CDCl_3$): δ 9.27 (s, 1H), 9.19 (br s, 1H), 8.23 (br t, J=4.8 Hz, 1H), 6.89 (d, J=8.4 Hz, 1H), 6.11 (dd, J=8.4 Hz, J=2 Hz, 1H), 6.06 (d, J=2 Hz, 1H), 5.71 (s, 1H), 3.69 (br s, 1H), 3.65 (br s, 2H), 3.11 (t, J=7.2 Hz, 2H), 3.06 (td, J=6.8 Hz, J=5.6 Hz, 2H), 1.67-1.57 (m, 4H), 1.42-1.27 (m, 20H), 0.90-0.87 (m, 6H). $^{13}C$ NMR (100 MHz, $CDCl_3$): δ 149.3, 148.8, 148.5, 143.8, 129.5, 129.0, 124.9, 124.3, 112.3, 104.6, 99.0, 92.9, 44.0, 43.1, 31.8, 31.7, 29.5, 29.4, 29.3, 29.2, 29.1, 28.3, 27.2, 26.9, 22.6, 14.1. HRMS (ESI-TOF): m/z $[M+H]^+$ for $C_{28}H_{45}N_6O_4^+$ calculated. 529.3497, found 529.3493, err. <1 ppm.

Compound PR4 according to the invention: $N^2$,$N^7$-dioctylphenazine-2,3,7-triamine

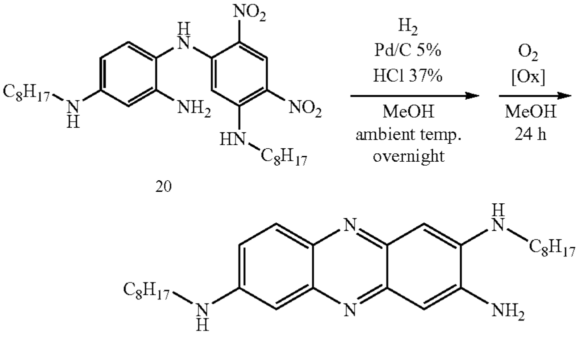

20

PR4

A solution of compound 20 (302 mg, 0.571 mmol) in MeOH (30 mL) was hydrogenated (20 bars) in the presence of Pd/C (5%) and HCl (12M, 0.5 mL) overnight. After addition of MeOH (30 mL), the solution was stirred under air for 24 h. The Pd/C was removed by filtration under Celite, and the solid phase was rinsed with MeOH (400 mL). The solution was neutralized with $NaHCO_3$ to pH 9 before adding water (100 mL). The solvent was concentrated to about 100 mL under reduced pressure. After cooling at 5° C. overnight, the resulting suspended solid was isolated by filtration and washed with water (2×30 mL), dried under vacuum to obtain compound PR4 (238 mg, 0.529 mmol, 93% yield) as a red powder. $^1H$ NMR (400 MHz, DMSO-$d_6$): δ 7.59 (d, J=9.2 Hz, 1H), 7.11 (dd, J=9.2 Hz, J=2.4 Hz, 1H), 6.79 (s, 1H), 6.59 (s, 1H), 6.58 (d, J=2.4 Hz, 1H), 6.22 (br t, J=4.8 Hz, 1H), 5.98 (br s, 2H), 5.65 (br t, J=4.4 Hz, 2H), 3.22 (td, J=6.8 Hz, J=5.2 Hz, 2H), 3.13 (td, J=6.8 Hz, J=5.6 Hz, 2H), 1.73-1.60 (m, 4H), 1.43-1.27 (m, 20H), 0.57-0.56 (m, 6H). $^{13}C$ NMR (100 MHz, DMSO-$d_6$): 147.6, 143.0, 141.2, 140.2, 138.5, 135.5, 128.2, 121.1, 102.5, 99.9, 99.4, 43.2, 42.8, 31.2, 28.9, 28.2, 27.9, 26.8, 26.8, 22.1, 13.9. HRMS (ESI-TOF): m/z $[M+H]^+$ for $C_{28}H_{44}N_5^+$ calculated. 450.3591, found 450.3590, err. <1 ppm.

PR5 Compound

Compound 21: N$^1$-(2,4-dinitro-5-(3,4,5-trimethoxyphenylamino)phenyl)-NA-octylbenzene-1,2,4-triamine

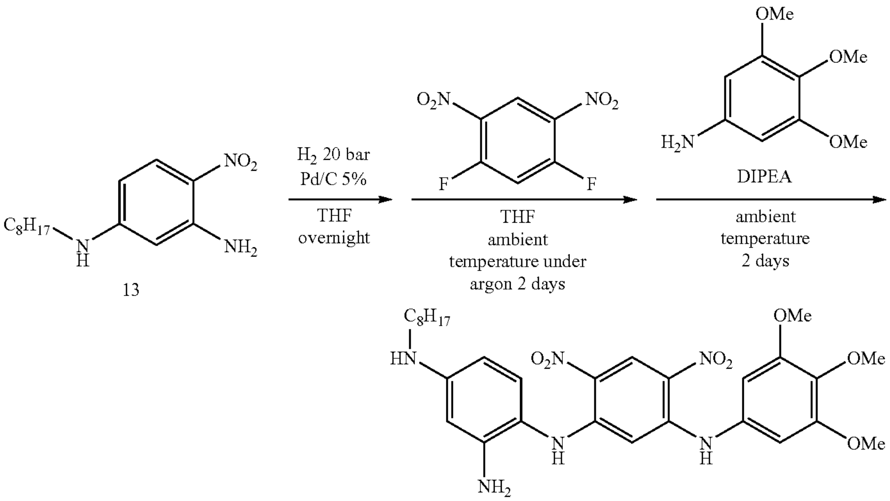

13

21

A solution of compound 13 (1.50 mg, 5.83 mmol, 1.0 eq) in THF (50 mL) was hydrogenated (20 bars) in the presence of 5% Pd/C (124 mg, 0.058 mmol, 1 mol %) overnight. Then the mixture was degassed by sonication for 5 min. After addition of DFDNB (1.10 g, 5.39 mmol, 0.92 eq), the reaction was stirred at room temperature under argon for 2 days. Then 3,4,5-trimethoxylaniline (2.20 g, 12 mmol, 2.23 eq) and DIPEA (600 μL, 3.44 mmol, 0.64 eq) were added to the reaction. The mixture was kept two more days at room temperature. The Pd/C was removed by filtration through Celite. After concentration in vacuo, the raw product was taken up in EtOH. The filtrate was concentrated and purified by column chromatography (silica 60F, AE/CH, 40/60) to obtain compound 21 (1.34 g, 2.30 mmol, 43% yield) in the form of a red solid. $^1$H NMR (400 MHz, $CDCl_3$): δ 9.73 (br s, 1H), 9.31 (s, 1H), 9.15 (br s, 1H), 6.75 (d, J=8.4 Hz, 1H), 6.37 (s, 2H), 6.28 (s, 1H), 5.95 (dd, J=8.4, 2.5 Hz, 1H), 5.90 (d, J=2.5 Hz, 1H), 3.79 (s, 3H), 3.76 (s, 6H), 3.61 (dps, 2H), 3.58 (dps, 1H), 3.00 (t, J=7.2 Hz, 2H), 1.58 (quintet, J=7.2 Hz, 2H), 1.40-1.29 (m, 10H), 0.90 (t, J=6.9 Hz, 3H). $^{13}$C NMR (100 MHz, $CDCl_3$): δ 153.7, 149.4, 149.0, 146.7, 143.7, 136.3, 133.0, 129.3, 128.7, 125.23, 125.16, 111.8, 104.3, 101.7, 98.6, 95.4, 60.9, 56.1, 43.9, 31.8, 29.49, 29.39, 29.25, 27.2, 22.6, 14.1. HRMS (ESI-TOF): m/z $[M+H]^+$ for $C_{29}H_{39}N_6O_7^+$ calculated. 583.2875, found 583.2878, err. <1 ppm.

PR5 compound: N$^7$-octyl-N$^2$-(3,4,5-trimethoxyphenyl)phenazine-2,3,7-triamine

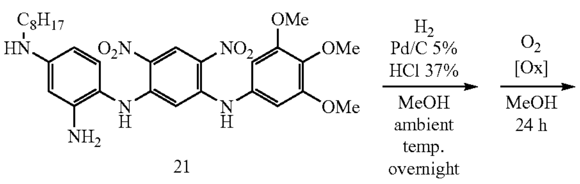

21

-continued

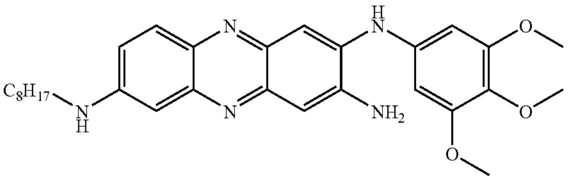

PR5

A solution of compound 21 (150 mg, 0.257 mmol) in MeOH (75 mL) was hydrogenated (20 bars) in the presence of Pd/C (5%) and HCl (12M, 0.5 mL) throughout the night. After addition of MeOH (30 mL), the solution was stirred under air for 24 h. The Pd/C was removed by filtration under Celite, and the solid phase was rinsed with MeOH (400 mL). The solution was neutralized with $NaHCO_3$ to pH 9 before adding water (100 mL). The solvent was concentrated to about 100 mL under reduced pressure. After cooling at 5° C. overnight, the resulting solid in suspension was isolated by filtration and washed with water (2x30 mL), dried under vacuum to obtain compound PR5 (110 mg, 0.218 mmol, 85% yield) as a red powder. $^1$H NMR (400 MHz, DMSO-$d_6$): δ 7.79 (d, J=9.2 Hz, 1H), 7.60 (br s, 1H), 7.23 (s, 1H), 7.05 (dd, J=9.2, 2.5 Hz, 1H), 6.89 (d, J=2.5 Hz, 1H), 6.38 (s, 2H), 5.56 (s, 1H), 4.28 (br s, 2H), 4.19 (br t, J=5.3 Hz, 1H), 3.85 (s, 3H), 3.82 (s, 6H), 3.28 (td, J=6.9, 5.5 Hz, 2H), 1.72 (quintet, 7.2 Hz, 2H), 1.48-1.25 (m, 10H), 0.89 (t, J=6.8 Hz, 3H). $^{13}$C NMR (100 MHz, DMSO-$d_6$): δ 153.3, 148.4, 144.30, 144.17, 142.1, 138.4, 137.0, 136.26, 136.06, 132.5, 128.7, 122.0, 108.2, 103.5, 98.7, 97.8, 60.1, 55.76, 55.59, 42.7, 31.2, 28.82, 28.68, 28.2, 26.7, 22.0, 13.9. HRMS (ESI-TOF): m/z $[M+H]^+$ for $C_{29}H_{38}N_5O_3^+$ calculated. 504.2969, found 504.2972, err. <1 ppm.

3—Synthesis Method No. 3-Compound of Formula II (1b)

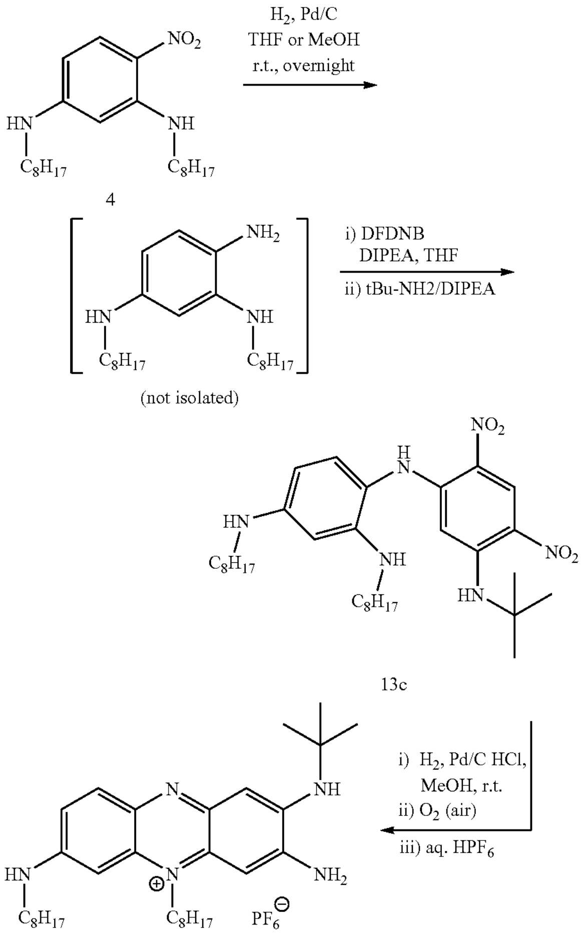

4

(not isolated)

13c

1b

Compound 13c: A solution of compound 4 (625 mg, 1.66 mmol, 1 equiv.) in THF (35 mL) was hydrogenated (40 bars) overnight in the presence of Pd/C (5 wt. %, 36 mg, 1 mol %). After decreasing the pressure, the solution was degassed by sonication for 5 min, then cooled to 0° C. in an ice tray, and 1,5-difluoro-2,4-dinitrobenzene (320 mg, 1.57 mmol, 0.95 equiv.) was added to the solution with stirring. Then tert-butylamine (736 µL, 6.98 mmol, 4.2 equiv.) and DIPEA (602 µL, 3.46 mmol, 2.1 equiv.) were added. The mixture was stirred at room temperature for 4 days. After filtration through celite via dichloromethane and evaporation of the solution, the raw product was purified by flash chromatography on silica gel using dichloromethane/cyclohexane (1/1 to 6/4) as eluent to obtain the compound 13c as a red solid (575 mg, 63% yield).

TLC: $R_f$=0.25 ($SiO_2$ F60, dichloromethane/cyclohexane, 7/3). $^1H$ NMR (400 MHz, $CDCl_3$): δ 9.26 (s, 1H), 9.00 (br s, 1H), 8.40 (br s, 1H), 6.86 (d, J=8.3 Hz, 1H), 5.99 (dd, J=8.3, 2.4 Hz, 1H), 5.95 (d, J=2.4 Hz, 1H), 5.90 (s, 1H), 3.81 (br s, 1H), 3.66 (br s, 1H), 3.12 (t, J=7.1 Hz, 2H), 3.07-3.03 (m, 2H), 1.66-1.59 (m, 2H), 1.56-1.50 (m, 2H), 1.44-1.22 (m, 29H), 0.89 (t, 6.9 Hz, 3H), 0.86 (t, 6.9 Hz, 3H). $^{13}C$ NMR (100 MHz, $CDCl_3$): δ 149.7, 148.4, 147.4, 145.4, 129.5, 129.0, 125.5, 124.0, 112.1, 101.5, 95.6, 95.1, 52.0, 44.1, 43.5, 31.8, 31.8, 29.5, 29.5, 29.4, 29.3, 29.3, 29.2, 29.0, 27.2, 27.1, 22.7, 22.6, 14.1, 14.1. HRMS (ESI-TOF): m/z $[M+H]^+$ for $C_{32}H_{53}N_6O_4^+$ calculated. 585.4123, found 585.4123, err. <1 ppm.

Compound 1b: A solution of compound 13c (1 g, 1.71 mmol, 1 equiv.) in methanol (60 mL) was hydrogenated (20 bars) in the presence of Pd/C (5% by mass) and HCl (12M, 0.5 mL) for 6 hours. Then the mixture was stirred under air for 16 h. The Pd/C was removed by filtration through celite (AW) that had been rinsed several times with methanol and dichloromethane. After removal of the solvent under reduced pressure, the resulting solid was taken up in dichloromethane and washed with an aqueous solution of $HPF_6$ (5% by mass in water, 2×60 mL) and distilled water (60 mL). The organic layer was dried with $Na_2SO_4$, filtered and evaporated under reduced pressure. The residue finally obtained was precipitated in pentane and filtered to obtain product 1b $[PF_6^-]$ in the form of a red solid (1.05 g, 95% yield).

$^1H$ NMR (250 MHz, $CD_3CN$, diluted): δ 7.85 (d, J=9.3 Hz, 1H), 7.24-7.20 (m, 2H), 6.99 (s, 1H), 6.57 (d, J=1.8 Hz, 1H), 6.28-6.20 (br m, 3H), 4.58 (d, J=8 Hz, 2H), 4.37 (br s, 1H), 3.37 (td, J=7.0 Hz, J=6.2 Hz, 2H), 1.75-1.55 (m, 4H), 1.52 (s, 9H), 1.46-1.31 (m, 20H), 0.92-0.87 (m, 6H). $^1H$ NMR (250 MHz, $CD_3CN$, concentrated): δ 7.76 (d, J=9.3 Hz, 1H), 7.20-7.15 (m, 2H), 6.96 (s, 1H), 6.49 (d, J=1.8 Hz, 1H), 6.34-6.29 (br m, 3H), 4.50 (d, J=8 Hz, 2H), 3.33 (m, 2H), 1.76-1.30 (m, 33H), 0.91-0.86 (m, 6H). $^{13}C$ NMR (63 MHz, $CD_3CN$, concentrated): 154.3, 152.4, 139.3, 137.8, 137.6, 134.1, 133.2, 131.3, 121.7, 109.6, 94.7, 90.3, 53.1, 48.8, 44.2, 32.5, 32.5, 30.0, 30.0, 29.9, 29.2, 29.1, 27.8, 27.5, 27.2, 23.3, 23.3, 14.3, 14.3. HRMS (ESI-TOF): m/z $[M+H]^+$ for $C_{32}H_{52}N_5^+$ calculated. 506.4217, found 506.4220, err. <1 ppm.

Example 2—Physicochemical Properties of the Compounds According to the Invention The inventors have identified the following different properties of the compounds according to the invention:

a. Solubility

The versatility of the synthesis method allows the introduction of various substituents ad infinitum to modulate the solubility properties. Depending on the hydrophilic/hydrophobic nature of R1, R2, R3 and R4, it is thus possible to solubilize type II compounds in polar, apolar, protic or aprotic solvents.

It is noted that although the compounds are more soluble in organic solvents, these exhibit the property of solubility in water, a property of major interest for use in vitro and in vivo on biological and cellular samples.

a. Characterization of Protonated Forms

The inventors have characterized the different protonated forms of compounds of formula I where $R_1$ and $R_2$ are $C_8H_{17}$, $R_3$ is tert-butyl and $R_4$ is H, of the following formula:

[Chem. 8]

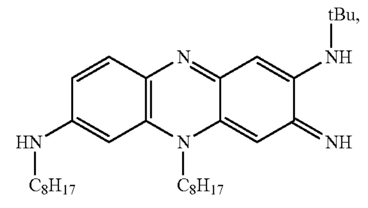

as well as the mono, di and tri protonated forms of the following respective formulas

[Chem. 5]

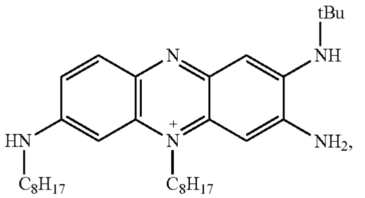

[Chem. 9]

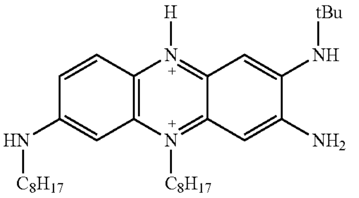

and

[Chem. 10]

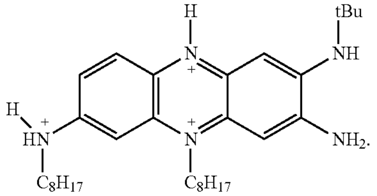

The results obtained are shown in FIG. 1.

The $^{1}H$ NMR spectra of the compound

[Chem. 5]

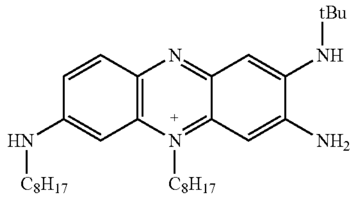

confirmed this hypothesis in particular with the presence of three protons, Ha, Hb and Hc, in the aromatic region with coupling constants traditionally encountered within a 1,2,4-trisubstituted benzene. $^{1}H$ NMR data also showed the presence of two magnetically non-equivalent octyl chains. All of these data suggest the formation of a *phenazinium* derivative In addition, the proton signals $H_d$ and $H_e$—respectively at δ=7.17 and 7.00 ppm—experience a very strong shielding effect ($\delta_{Hd}$=6.25 ppm and ($\delta_{He}$=5.91 ppm) after addition of NaOD (40% w/w in $D_2O$), an effect that is unusually observed within an aromatic system but already seen within certain triaminophenazines (δ=6.5-6.1 ppm and 5.9-5.4 ppm) described by Roy. This observation can be explained by a deprotonation reaction inducing a break in aromaticity in favor of a quinoidal-type structure a. Optical Properties In addition to characterizing the protonated forms, the inventors also tested the absorption and emission properties of the various compounds according to the invention.

i) Absorption Properties

The inventors tested the absorption of the four more or less protonated compounds mentioned above and evaluated ε ($M^{-1}$ $cm^{-1}$) as a function of the wavelength λ (in nm).

FIG. 2 shows the absorption spectrum of the type I molecule. The absorption spectrum reflects the presence of an uncharged type I species for which the degree of delocalization/conjugation is lower (hypsochrome effect) than for the type II cationic species.

FIG. 3 shows the absorption spectrum of the type II molecule. The absorption spectrum reflects the presence of a mono-charged type II species for which the degree of delocalization/conjugation is greater (batochromic effect) than for the neutral type I species.

FIG. 4 shows the absorption spectrum of the C-type molecule. A "super" acid, triflic acid (HOTf) ($pKa_{(MeCN)}$ =0.70), was used to protonate II in the UV cell (C=1.44×$10^{-5}$ M, in MeCN). When acid is added (from 0.1 to 16 equiv.), the intensity of the initial bands located at 267, 308, 465 and 552 nm decreases in favor of the appearance of new bands at 274, 322, 507 and 686 nm. This spectral evolution reflects the disappearance of the starting compound II in favor of the formation of a single type C species whose absorption bands are of higher energy. The first protonation step is complete after adding 16 equiv. of HOTf FIG. 5 shows the absorption spectrum of the D-type molecule. Beyond the addition of 16 equiv. of triflic acid, a new species appears (new bands at 268, 287, 370, 475 and 506 nm) at the same time as the C cation disappears. Double protonation of II is complete after adding plus 2600 equiv. of HOTf. The C band at 686 nm has completely disappeared in favor of the spectrum of a D trication having a narrow band at 506 nm and equipped with a shoulder characteristic of a cyanine-type structure.

ii) Emission Properties

The inventors tested the fluorescence emission as a function of the wavelength λ (in nm) for the following compound taken up in acetonitrile

[Chem. 5]

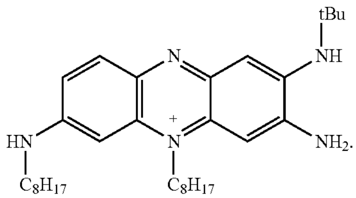

The results obtained are shown in FIG. 6.

The UV-Vis absorption spectrum of II showed the presence of two main bands located at $\lambda_{max}$=265 nm and 549 nm and with respective shoulders located at λ=295 nm and 578 nm. Molecule II is also fluorescent and emits at $\lambda_{em}$=642 nm (excitation at)=550 nm). This emission is comparable to that produced by the "neutral red" cationic analogue compound reported in the literature ($\lambda_{abs}$=534 nm and $\lambda_{em}$=616 nm)

iii) Fluorescence Yield and Emission

The inventors then set out to measure the value Φf of the quantum yield of fluorescence of the following compound taken up in acetonitrile

[Chem. 5]

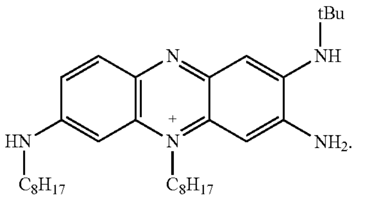

To do this, the inventors measured the absorbance (relative intensity) as a function of the wavelength (in nm) in the presence of increasing doses of 1,8-DiazaBicyclo[4.3.0] Undec-7-ene (DBU-0 to 2 equivalents).

The results are shown in FIG. 7.

*Phenazinium* II and its II-H conjugate base fluoresce in MeCN at neutral or basic pH. Conversely, no luminescence property was observed in an acid medium. FIG. 7 shows the spectral evolution of *phenazinium* II during the addition of DBU (excitation at 483 nm). This evolution clearly reflects the disappearance of the starting compound (decrease in the band at 637 nm) in favor of the formation of a single II-H species possessing an emission at higher energy much lower than that of II (increase in the band at 550 nm). Calculations of quantum yields indeed show that the deprotonated form [II-H] produces less fluorescence ($\Phi_f$=0.08 at 550 nm) than the starting form II ($\Phi_f$=0.76 at 637 nm). The reference used for the calculation of the fluorescence quantum yield is tetraphenylporphyrin in acetonitrile ($\Phi_f$=0.15).

The emission maximum is at a localized wavelength in the far red at 645 nm.

The coefficient Φf found is 0.76, which attests to a very high fluorescence yield and a high brightness of about 50000.

The brightness (B) is proportional to the amount of light emitted by fluorescence at a given excitation light according to the relationship B=ε×Φ(with ε=molar extinction coefficient and Φ the emission quantum yield).

The calculation of ε is carried out using a spectrophotometer measuring the absorbance A (quantity without unit) of a dilute solution of known concentration C in a tank of thickness I.

The fundamental relation used in spectrophotometry is presented in the form: A=ε·I·c (A being the absorbance or optical density)

Calculation of Φ: It is determined by measuring the emission intensity of a solution of known concentration; the reference used to calculate the fluorescence quantum yield here is tetraphenylporphyrin in acetonitrile ($\Phi_f$=0.15).

The quantum yield is defined by:

Φ=number of photons emitted/number of photons absorbed iv) Fluorescence In Vivo

Prior to fluorescent labeling tests on cell lines, the inventors tested the toxicity of the compounds according to the invention.

MCF-7 cancer lines were seeded in 96-well plates at a concentration of approximately 5000 cells/well in 200 μl of culture medium and left in culture for 24 hours. Then, the cells were incubated for 72 h, with or without the compound to be tested (from 1 nM to 1 μM). After incubation with the compounds, an MTT test was carried out in order to test the cytotoxicity of the compounds. The cells were briefly incubated in the presence of 0.5 mg mL-1 of MTT for 4 h in order to measure mitochondrial activity. Then, the MTT precipitates were dissolved in 150 μL of an ethanol/DMSO (1:1) mixture solution and the absorbance was read at 540 nm.

The inventors came to the conclusion that the 100 nM dose did not significantly affect cell survival, as shown in FIG. 14. It is observed very clearly that the cytotoxicity in the dark is low at a concentration of 100 nM (FIG. 14)

The inventors tested the fluorescence of the compound of the following formula

[Chem. 5]

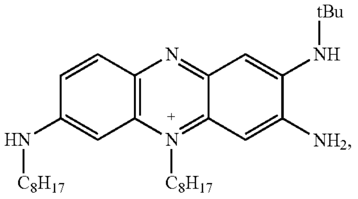

on MCF-7 breast cancer cells by single-photon (excitation at 514 nm) or two-photon (excitation at 790 or 810 nm) microscopy.

One- and Two-Photon Imaging

The MCF-7 human breast cancer cells were seeded in petri dishes (World Precision Instrument, Stevenage, UK) having a glass plate at the bottom, in 2 mL of culture medium. The cells were then incubated for 16 h with the compound according to the invention at a concentration of 0.1 μM or 0.5 μM. 15 minutes before the end of the incubation, the cells were incubated with Hoechst 33342 (Invitrogen, Cergy Pontoise, France) at a final concentration of 5 μg·mL$^{-1}$ in order to label the cell nuclei. Then the cells were washed twice with culture medium.

One-photon fluorescence imaging was performed on live cells at a wavelength of 514 nm using a Carl Zeiss Confocal Microscope (LSM780). Two-photon fluorescence imaging was performed at wavelengths of 790 nm or 810 using the Chameleon laser available on the same microscope. All images were taken with the same objective, at the same magnification (63×/1.4 OIL DIC Plan-Apo).

The results obtained in single-photon microscopy are presented in FIG. 8, and in two-photon microscopy in FIG. 9.

These compounds showed remarkable one- and two-photon imaging properties (FIGS. 3 and 4). It clearly appears that the compounds are easily identifiable and that their localization is only cytoplasmic (the co-localizations are perfectly conclusive). It is interesting to note that the clearest and most intense markings are obtained with the lowest concentrations. Indeed, the markings are clearly finer and reveal intense cytoplasmic granules, which tends to show that a more precise identification of cytoplasmic targets is possible under these conditions. In particular, intense fluorescence foci obtained in perinuclear regions may correspond to the endoplasmic reticulum.

The inventors also tested the internalization of the compounds according to the invention over time.

The internalization kinetics were carried out with a CLARIOstar reader in order to quantify the internalization of the compound in the MCF-7 tumor cells. The values, corresponding to the ratio of the residual fluorescence/the total fluorescence, are presented in the form of means of three experiments, + the standard deviation.

It is clearly seen (FIG. 10) that 10% of the fluorescent compound (II) penetrates the cell in less than 24 hours, allowing observation of very high-quality images.

The kinetics of incorporation by MCF-7 cells is shown in FIG. 10.

a. $^1O_2$ Output

The absorption spectra were measured with a Perkin-Elmer double beam UV-visible spectrophotometer (Lambda EZ 210). The fluorescence spectrum was measured with a Fluorolog FL3-222 spectrofluorimeter (Horiba Jobin Yvon, Longjumeau, France) equipped with a 450 W xenon arc lamp, a thermostated compartment (25° C.), a photomultiplier UV-visible R928 (HAMAMATSU Japan) and an InGaAs infrared detector cooled with liquid nitrogen (DSS-16A020L Electro-Optical System Inc, Phoenixville, PA, USA). The excitation beam is separated by an SPEX dual grating monochromator (1200 lines/mm blazed at 330 nm). The fluorescence was measured by the UV-Visible detector via the SPEX double grating emission monochromator (1200 lines/mm blazed at 500 nm). The production of singlet oxygen was measured by the infrared detector via the SPEX double grating emission monochromator (600 lines/mm blazed at 1 μm). All spectra were measured using 4-sided quartz cuvettes. The absorbance values at the excitation wavelength of the references and samples have been adjusted to approximately 0.2.

By this method, the inventors were able to measure the quantum yield DA, which is 0.11 for the compound

[Chem. 5]

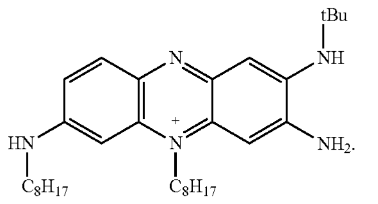

This low efficiency is expected, since the vast majority of absorbed photons are converted into light, about 76% of photons.

Example 3—Use of the Compounds According to the Invention in Photodynamic Therapy In Vitro The inventors tested the effect of the compounds according to the invention in photodynamic therapy. MCF7 cells were incubated with the compound of formula

[Chem. 5]

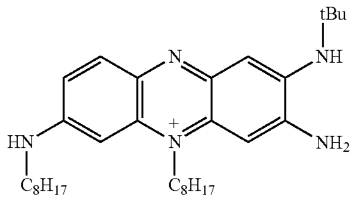

for 5 h and irradiated (or not) at 530 nm for 20 minutes. Two days later, the cells were subjected to a colorimetric cell viability assay (MTT).

The results are presented in FIGS. 12 and 13.

The results obtained under one-photon irradiation ($\lambda_{irrad.}$=514 nm) are exceptional, since 98% of tumor cells are killed at very low concentrations (C=100 nM).

As can be seen in FIG. 13, at a concentration of 100 nM, two zones are easily distinguished owing to the violet crystals of MTT, which only stain living cells (not irradiated).

Two-photon photodynamic therapy ($\lambda_{irrad.}$=810 nm) has shown very encouraging results, since nearly 50% of tumor cells are killed without optimization (irradiation for only 5 seconds at a very low concentration of 100 nM of compound according to the invention).

The inventors also tested the effect of the compounds according to the invention in photodynamic therapy on other models. Keratosis treatment tests were carried out at different concentrations of a photosensitizing compound (PS): either that used on the MCF-7 cells, or the compound of formula

[Chem. 6]

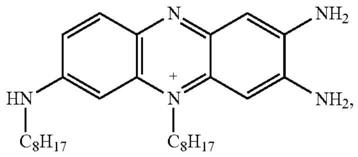

on cultured keratinocytes. PS was added to the cells for 20 minutes at doses of 0 nM (A), 10 nM (B), 25 nM (C) or 50 nM (D) and the latter were irradiated (black columns) or not (gray columns) at 530 nm (FIGS. 15 and 17). Two days later, the cells are subjected to a colorimetric cell viability assay (MTT) (FIGS. 16 and 18).

Example 4—Internalization of the Compounds According to the Invention

The inventors evaluated the capacity of the cells to internalize the compounds according to the invention.

To do this, MCF-7 cells or healthy donor fibroblasts have been treated or not with 0.5 nM of compound of formula

[Chem. 5]

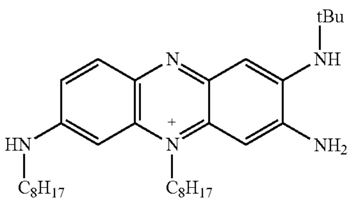

for 1, 3, 6 or 24 h, and cell fluorescence was assessed by flow cytometry by detecting the number of cells with red fluorescence.

The results can be seen in FIGS. 20 and 21.

At an equal concentration (0.5 nM) after 6 h of incubation with the compound according to the invention, 46% of the cancerous cells (MCF-7) have internalized the compound, but only 18% of the healthy cells (fibroblasts) have. Similarly, 90% of cancer cells have internalized the compound according to the invention after 24 h compared with only 24% for healthy cells.

These results show that the compound according to the invention enters cancerous cells more rapidly than it enters healthy cells.

Example 5—Comparison Absorption of *Phenazinium* According to the Invention and Phenazine Described in the Prior Art

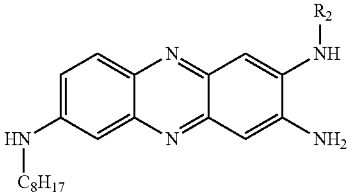

24: $R_2 = C_8H_{17}$ (93%)

25: $R_2$ = 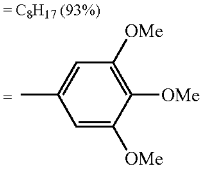 (85%)

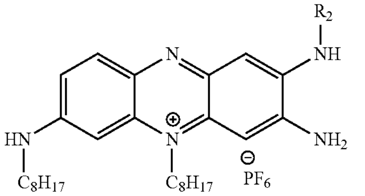

12•[FP6]: $R_2$ = tBu (90%)
23•[PF6]: $R_2 = C_8H_{17}$ (87%)

The cationic phenaziniums ($[12]^+$; $[23]^+$) are much more soluble than the neutral phenazines (24 and 25). The latter are indeed insoluble in alcohols and poorly soluble ($C<10^{-4}$ M) in MeCN, or acetone, whereas cationic phenaziniums ($[12]^+$; $[23]^+$) are soluble in all common solvents (i.e. toluene, $Et_2O$, $CH_2CL_2$, $CHCl_3$, acetone, MeCN, MeOH, EtOH DMF, DMSO) due to their amphiphilic character (the charged part being hydrophilic and the alkylated part being hydrophobic).

The absorption spectra of the compounds ($[12]^+$; $[23]^+$) are almost identical and show a band located in the region visible at $\lambda_{max}$=553 nm ($\varepsilon^{543}$=43400 $M^{-1}$ $cm^{-1}$ and $\varepsilon^{543}$=41200 $M^{-1}$ $cm^{-1}$) with a shoulder around 465 nm. Two absorption bands located in the ultraviolet at 265 nm and 320 nm complete these absorption spectra.

The absorption characteristics of the phenazine compounds 24 and 25 are similar to those of the cationic *phenazinium* compounds with, however, a 100 nm blue shift, their absorption appearing respectively at $\lambda_{max}$=472 nm ($\varepsilon^{472}$=16100 $M^{-1}$ $cm^{-1}$) and $\lambda_{max}$=472 nm ($\varepsilon^{472}$=14800 $M^{-1}$ $cm^{-1}$). The corresponding intensities are conversely much weaker (35 to 45% of the intensity of the main peak of the cationic *phenazinium* compounds). Furthermore, compounds 24 and 25 show several additional absorption bands located between 220 and 300 nm.

The data is shown in FIG. 19.

This demonstrates that *phenazinium* compounds are more suitable for photon therapy than neutral phenazines because they are more soluble and can be irradiated with a lower-energy laser (longer excitation wavelengths).

The invention claimed is:

1. A compound of the following formula I:

(I)

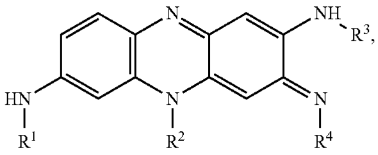

where, independently of each other, R1 and R2 are:

either a linear or branched, saturated or unsaturated, cyclic or non-cyclic C1-C18 alkyl, optionally substituted by one or more groups chosen from a hydroxyl group, an amino group, an aminoalkyl group, a C1-C5 alkoxy group, a C1-C5 alkyl, a peptide, a pyridine group, a phosphine group, a thiol, a C2 alkene, a C2 alkyne group and a halogen, or a benzyl radical optionally substituted by one or more radicals chosen from a hydroxyl group, an amino group, an aminoalkyl group, a C1-C5 alkoxy group, a C1-C5 alkyl group, and a halogen, or (hetero) aryl groups, optionally substituted by one or more groups chosen from a hydroxyl group, an amino group, an aminoalkyl group, a C1-C5 alkoxy group, a C1-C5 alkyl, a peptide, a pyridine group, a phosphine group, a thiol, a C2 alkene, a C2 alkyne group and a halogen, or a benzyl radical optionally substituted by one or more radicals chosen from a hydroxyl group, an amino group, an aminoalkyl group, a C1-C5 alkoxy group, a C1-C5 alkyl group, and a halogen, and independently of each other, R3 and R4 are selected from the group consisting of H, R1 and R2, or R3 and R4 are either or both a carbonyl functional group forming amine functions, or a salt or solvate thereof, or a protonated form thereof.

2. The compound according to claim 1, wherein R1 and R2, independently of one another, are linear or branched, saturated or unsaturated, cyclic or non-cyclic C4-C10 alkyls.

3. The compound according to claim 1, wherein the protonated form of the compound of formula 1 is chosen from the following compounds:

the compound of formula Ia:

[Chem. 2]

(Ia)

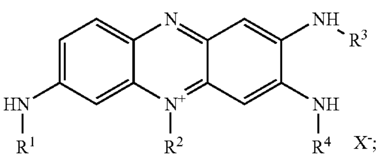

the compound of formula Ib:

[Chem. 3]

(Ib)

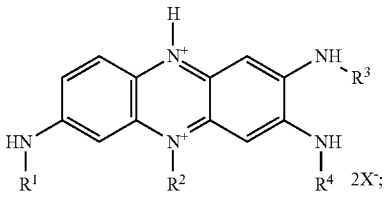

and the compound of formula Ic:

[Chem. 4]

(Ic)

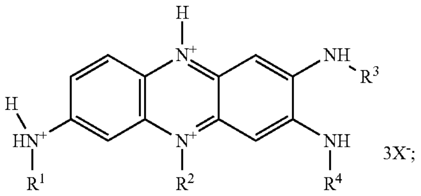

where X represents Cl, Br, OH, F, I, $BF_4$ or $PF_6$ or trifluoromethanesulfate (Otf).

4. The compound according to claim 1, said compound having the following formula II or III:

[Chem. 5]

(II)

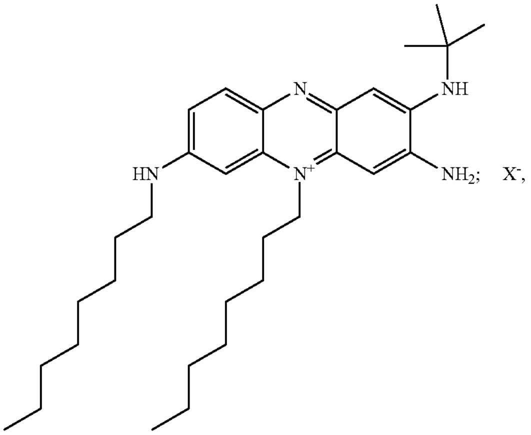

[Chem. 6]

(III)

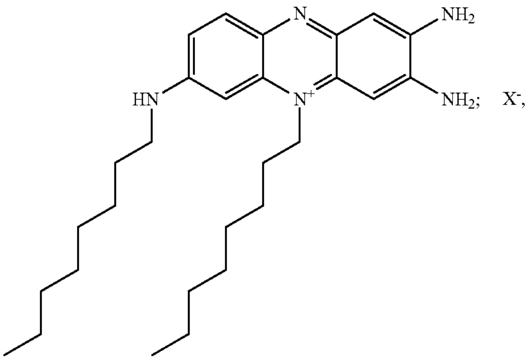

-continued

[Chem. 7]

(IV)

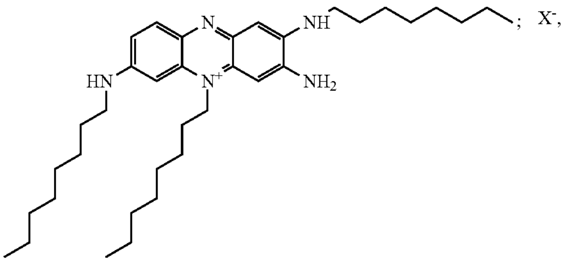

where X represents Cl, Br, OH, F or I.

5. The compound according to claim 1, wherein R3 and R4 are either or both a carbonyl functional group forming amine functions including peptides.

6. A pharmaceutical composition comprising, as active substance, a compound according to claim 1, in association with a pharmaceutically acceptable vehicle.

7. A method for treating a pathology by photodynamic therapy comprising administering an effective amount of a compound according to claim 1 to a patient in a need thereof.

8. The method according to claim 7, wherein said pathology is a tumor.

9. A method for diagnosing cancer, comprising administering to an individual liable to be afflicted by a cancer a compound according to claim 1, and detecting one or two photon fluorescence.

10. A method for visualizing living cells, cytoplasmic or tissues, by fluorescence microscopy, comprising:

bringing the living cells, the cytoplasmic organelles or the tissues, into contact with a compound according to claim 1, at a concentration of 2 to 500 $nmol \cdot L^{-1}$, to obtain marked living cells, cytoplasmic organelles or tissues, exposing marked living cells, cytoplasmic organelles or tissues to a light beam having a wavelength varying from 450 to 850 nm, and detecting by appropriate one- or two-photon fluorescence detection means of the fluorescent emitted by the marked living cells, cytoplasmic organelles or tissues.

11. A method for eradicating a cell comprising:

contacting the cell with a compound according to claim 1, in order to obtain a contacted cell, exposing the contacted cell with a light source emitting one or two photons, wherein the compound being used at a concentration varying from 1 to 1000 $nmol \cdot L^{-1}$.

* * * * *